US007879800B2

(12) United States Patent
Bauer

(10) Patent No.: US 7,879,800 B2

(45) Date of Patent: Feb. 1, 2011

(54) LARGE SCALE PREPARATION OF ALPHA-1 PROTEINASE INHIBITOR AND USE THEREOF

(75) Inventor: Shabtai Bauer, Jerusalem (IL)

(73) Assignee: Kamada Ltd., Rehovot (IL)

( * ) Notice: Subject to any disclaimer, the term of this patent is extended or adjusted under 35 U.S.C. 154(b) by 1040 days.

(21) Appl. No.: 10/572,523

(22) PCT Filed: Sep. 22, 2004

(86) PCT No.: PCT/IL2004/000881

§ 371 (c)(1), (2), (4) Date: Jan. 19, 2007

(87) PCT Pub. No.: WO2005/027821

PCT Pub. Date: Mar. 31, 2005

(65) Prior Publication Data

US 2008/0139465 A1 Jun. 12, 2008

Related U.S. Application Data

(60) Provisional application No. 60/503,902, filed on Sep. 22, 2003.

(30) Foreign Application Priority Data

Sep. 22, 2003 (IL) ..................................... 158053

(51) Int. Cl.
*A61K 38/00* (2006.01)
*C07K 1/30* (2006.01)
*C12N 7/06* (2006.01)

(52) U.S. Cl. ......................... 514/12; 530/419; 530/420; 530/421; 435/238

(58) Field of Classification Search ....................... None
See application file for complete search history.

(56) References Cited

U.S. PATENT DOCUMENTS

| | | | | |
|---|---|---|---|---|
| 4,379,087 | A | 4/1983 | Coan | 530/380 |
| 4,439,358 | A | 3/1984 | Coan et al. | 530/392 |
| 4,629,567 | A | 12/1986 | Bollen et al. | 210/635 |
| 4,656,254 | A | 4/1987 | Shearer et al. | 530/393 |
| 4,697,003 | A | 9/1987 | Coan | 530/380 |
| 4,749,783 | A | 6/1988 | Jordan et al. | 530/393 |
| 4,857,317 | A | 8/1989 | Wijnendaele et al. | 424/227.1 |
| 5,093,316 | A | 3/1992 | Lezdey et al. | 514/8 |
| 5,455,330 | A | 10/1995 | Haskill et al. | 530/350 |
| 5,610,285 | A | 3/1997 | Lebing et al. | 530/416 |
| 5,780,440 | A | 7/1998 | Lezdey et al. | 514/21 |
| 6,093,324 | A * | 7/2000 | Bertolini et al. | 210/635 |
| 6,093,804 | A | 7/2000 | Ralston | 530/416 |
| 6,194,553 | B1 | 2/2001 | Lee et al. | 530/413 |
| 6,284,874 | B1 | 9/2001 | Taniguchi et al. | 530/420 |
| 6,462,180 | B1 * | 10/2002 | Lebing et al. | 530/395 |
| 6,525,176 | B1 | 2/2003 | Lee et al. | 530/350 |
| 6,974,792 | B2 | 12/2005 | Mattes et al. | 514/2 |
| 7,323,553 | B2 | 1/2008 | Fahrner et al. | 530/412 |
| 2004/0124143 | A1 | 7/2004 | Kee et al. | 530/412 |
| 2006/0194300 | A1 | 8/2006 | Schulz et al. | 530/412 |
| 2006/0234226 | A1 | 10/2006 | Fahrner et al. | 435/6 |
| 2007/0299251 | A1 | 12/2007 | Lihme et al. | 530/416 |

FOREIGN PATENT DOCUMENTS

| | | | |
|---|---|---|---|
| WO | 97/09350 | A1 | 3/1997 |
| WO | WO 97/48422 | | 12/1997 |
| WO | WO 98/56821 | | 12/1998 |
| WO | 00/17227 | A1 | 3/2000 |
| WO | WO 00/17227 | | 3/2000 |
| WO | 02/48176 | A1 | 6/2002 |
| WO | WO 03/102132 | | 12/2003 |
| WO | WO 2004/060528 | | 7/2004 |

OTHER PUBLICATIONS

Wright G. et al., "High level expression of active human alpha-1-antitrypsin in the milk of transgenic sheep". Biotechnology (N Y). Sep. 1991;9(9):830-834.

Archibald et al., "High-level expression of biologically active human alpha 1-antitrypsin in the milk of transgenic mice". Proc Natl Acad Sci U S A. Jul. 1990;87(13):5178-82.

Kress et al., "Large scale purification of alpha-1 trypsin inhibitor from human plasma". Prep Biochem. 1973;3(6):541-52.

Glaser et al., "Isolation and characterization of alpha-1-antitrypsin from the Cohn fraction IV-I of human plasma". Prep Biochem. 1975;5(4):333-48.

Podiarene et al., "Immunoaffinity purification of alpha 1-protease inhibitor from human plasma". Vopr. Med. Khim. Sep.-Oct. 1989;35(5):96-99.

(Continued)

*Primary Examiner*—Manjunath N Rao
*Assistant Examiner*—Kagnew H Gebreyesus
(74) *Attorney, Agent, or Firm*—Winston & Strawn LLP

(57) ABSTRACT

A process suitable for processing scaled-up amounts of source material in the range of tens of kilograms for the purification of alpha-1 proteinase inhibitor (API) from a mixture of unpurified proteins is provided. More particularly, a process for the purification of API from blood plasma or from plasma fractions to obtain pharmaceutical grade API on a commercial scale is provided. The API produced by the process is highly pure (at least 90% API out of the total protein) and highly active (at least 90% active API). Pharmaceutical compositions comprising the purified API and methods of using same are also described.

38 Claims, 5 Drawing Sheets

OTHER PUBLICATIONS

Burnouf T. et al., "Biochemical and biological properties of an alpha 1-antitrypsin concentrate". Vox Sang. 1987;52(4):291-297.

Hein RH. et al., "Production of alpha 1-proteinase inhibitor (human)". Eur Respir J Suppl. Mar. 1990;9:16s-20s.

Dubin A. et al., "Isolation of nine human plasma proteinase inhibitors by sequential affinity chromatography". Prep Biochem. 1990;20(1):63-74.

Wewers MD., "Comparison of alpha-1-antitrypsin levels and antineutrophil elastase capacity of blood and lung in a patient with the alpha-1-antitrypsin phenotype null-null before and during alpha-1-antitrypsin augmentation therapy". Am Rev Respir Dis. Mar. 1987;135(3):539-543.

Hubbard RC. et al., "Strategies for aerosol therapy of alpha 1-antitrypsin deficiency by the aerosol route". Lung. 1990;168 Suppl:565-578.

Translated Opposition against European Patent 1 664 123 B1 (Nov. 19, 2009).

Response filed on Nov. 19, 2009, in response to the Communication of Notices of Opposition against European Patent 1 664 123 B1.

* cited by examiner

LARGE SCALE PREPARATION OF ALPHA-1 PROTEINASE INHIBITOR AND USE THEREOF

This application is a national stage application of International Patent Application No. PCT/IL2004/000881 filed Sep. 22, 2004, which claims priority from U.S. Provisional Patent Application No. 60/503,902 filed Sep. 22, 2003.

FIELD OF THE INVENTION

The present invention relates to a process for the purification of alpha-1 proteinase inhibitor (API) from a mixture of proteins, to compositions comprising same and use thereof. More particularly, the present invention relates to a process for the large scale purification of API from blood plasma or from plasma fractions to obtain pharmaceutical grade API. The present invention also relates to formulations comprising the purified API, specifically ready to use liquid formulations and methods of using same.

BACKGROUND OF THE INVENTION

Certain human plasma proteins useful for therapeutic purposes and other applications can be obtained only from pooled blood donations. Recombinant production of plasma proteins is complicated by the fact that these proteins require accurate glycosylation patterns in order to maintain their function and/or half-life in the human body. Therefore even with the attendant risks of viral or other contamination the only approved available source for some proteins such as alpha 1 proteinase inhibitor is human plasma itself.

Alpha-1 proteinase inhibitor (API) is a derivative of human plasma belonging to the family of serine proteinase inhibitors. It is a glycoprotein having an average molecular weight of 50,600 daltons, produced by the liver and secreted into the circulatory system. The protein is a single polypeptide chain, to which several oligosaccharide units are covalently bound. API has a role in controlling tissue destruction by endogenous serine proteinases, and is the most prevalent serine proteinase inhibitor in blood plasma. Among others, API inhibits trypsin, chymotrypsin, various types of elastases, skin collagenase, renin, urokinase and proteases of polymorphonuclear lymphocytes.

API is currently used therapeutically for the treatment of pulmonary emphysema in patients who have a genetic deficiency in API. Purified API has been approved for replacement therapy in these patients. The normal role of API is to regulate the activity of leukocyte elastase, which breaks down foreign proteins present in the lung. When API is not present in sufficient quantities to inhibit elastase activity, the elastase breaks down lung tissue. In time, this imbalance results in chronic lung tissue damage and emphysema.

API was also proposed as a treatment for patients homozygous for the defective cystic fibrosis (CF) transmembrane conductance regulator (CFTR) genes, who suffer from recurrent endobronchial infections and sinusitis, malabsorption due to pancreatic deficiency, obstructive hepatobiliary disease and reduced fertility. The major cause of morbidity and mortality among CF patients is lung diseases. CFTR regulates transport of water and salts in the epithelial cells which cover internal and external surfaces of the body. In CF patients, the CTFR protein is defective due to a mutation, resulting in a defective water and salt transport and the production of thick secretions in several organs (e.g. lung, pancreas).

The membrane defect caused by the CFTR mutation leads to chronic lung inflammation and infection. Chronic lower respiratory infection provokes a persistent inflammatory response in the airway, resulting in chronic obstructive disease. As pulmonary reserves decrease, CF patients become prone to episodes of exacerbation, characterized by worsening symptoms of respiratory infection, particularly by *Peusdomonas aeruginosa*, accompanied by acute decline in lung function. In normal individuals, elastase secreted by neutrophils in response to infection is neutralized by API, which is known to penetrate into pulmonary tissue. In patients with CF, however, the unregulated inflammatory response overwhelms the normal protease (elastase)/antiprotease (API) balance. The abnormal cycle is destructively self-perpetuating and self-expanding: increased elastase leads to the recruitment of more neutrophils to the lung, which in turn secrete additional proteases. This leads to the accumulation of elastase in the lung and ultimately to tissue damage, destruction of the lung architecture, severe pulmonary dysfunction and, ultimately, death. It is suggested that supplement of additional API may reduce the deleterious effects associated with excessive amounts of elastase. The demand for API already exceeds the availability of the current supply, and this problem may become more pronounced as research suggests additional therapeutic uses for API. In order to maximize the available supply of API, a process for purifying API from human plasma should have the highest yield possible, and alternative sources should be also considered. Therefore, more efficient means of isolation, suitable for GMP (good manufacture practice) large-scale production, is required.

Several groups have reported production of recombinant API. (For example, G. Wright et al., Biotechnology, Vol. 9, pp. 830-834 (1991); A. L. Archibald et al., Proc. Nat'l. Acad. Sci. USA., Vol. 87, pp. 5178-5182 (1990)). However, at present, human plasma is the only approved source of therapeutic API.

Various methods of purifying API from human plasma have been described. The majority of these methods are directed to laboratory scale isolation while others pertain to production on a commercial level. Several methods of isolation are disclosed, for example in U.S. Pat. Nos. 4,379,087 and 5,610,285. Many early methods employed ammonium sulfate precipitation from human plasma followed by dialysis, further employing chromatographic step on DEAE-cellulose. However, the methods described for dialysis are not easily applicable to large-scale purification, and are lengthy, time-consuming processes likely to compromise the activity of the isolated protein.

A large-scale purification of API from human plasma was disclosed by Kress et al., (Preparative Biochem., 3:541-552, 1973)). The precipitate from the 80% ammonium sulfate treatment of human plasma was dialyzed and chromatographed on DEAE-cellulose. The concentrate obtained was again dialyzed and gel filtered on SEPHADEX™ G-100. The API-containing fractions were chromatographed twice on DE-52 cellulose to give API.

Glaser et al., (Preparative Biochem., 5:333-348, 1975) isolated API from Cohn Fraction IV-1 paste. In this method, dissolved IV-1 fraction was chromatographed on DEAE-cellulose, QAE-SEPHADEX™, concanavalin-A-SEPHAROSE™, and SEPHADEX™-G-150 to give API. However, Glaser et al. achieved only a 30% overall yield from fraction IV-1 paste.

Podiarene et al., (Vopr. Med. Khim. 35:96-99, 1989) reported a single step procedure for isolation of API from human plasma using affinity chromatography with monoclonal antibodies. API specific activity was increased 61.1 fold with a yield of only 20% from plasma.

Burnouf et al., (Vox. Sang. 52:291-297, 1987) starting with Cohn Fraction effluent II+III used DEAE chromatography and size exclusion chromatography to produce an API 80-90% pure (by SDS-PAGE) with a recovery of 65-70% from this effluent.

Hein et al., (Eur. Respir. J. 9:16s-20s, 1990) presented a process that employs Cohn Fraction IV-1 paste as the starting material and utilized fractional precipitation with polyethylene glycol followed by anion exchange chromatography on DEAE-Sepharose™. The final product has a purity of about 60% with 45% yield from IV-1 paste.

Dubin et al., (Prep. Biochem. 20:63-70, 1990) used a two-step chromatographic purification whereby alpha-PI, $C_1$-inhibitor, alpha-1 antichymotrypsin, and alpha-1 trypsin inhibitor were first eluted from Blue Sepharose™ and then API was purified by gel filtration. Purity and yield data were not given.

U.S. Pat. No. 4,749,783 discloses a method where biologically inactive proteins in a preparation were removed by affinity chromatography after a viral inactivation step. The basis of the separation between the native and denatured forms of the protein was the biological activity of the native protein towards the affinity resin and not physical differences between the native and denatured proteins.

An integrated plasma fractionation system based on polyethylene glycol (PEG) was disclosed by Hao et al. (Proceedings of the International Workshop on Technology for Protein Separation and Improvement of Blood Plasma Fractionation, Sep. 7-9, 1977, Reston, Va.). In the published method Cohn cryoprecipitate was mixed with increasing concentrations of PEG in order to obtain four different PEG fractions. The four fractions obtained were 0-4% PEG precipitate, 4-10% PEG precipitate, 10-20% PEG precipitate and 20% PEG supernatant. The 20% PEG supernatant fraction was dominated by albumin but also contained most of the API. However, this fraction also contained numerous other proteins, including all of the alpha-1-acid glycoprotein, antithrombin III, ceruloplasmin, haptoglobin, transferrin, Cl esterase inhibitor, prealbumin, retinol binding protein, transcortin, and angiotensinogen.

Several other groups have combined PEG precipitation with other purification methods in an attempt to isolate API. For instance, U.S. Pat. Nos. 4,379,087; 4,439,358; 4,697,003 and 4,656,254, all employ a PEG precipitation step in processes of isolating API. However, the disclosed methods do not attempt to separate active from non-active API.

Japanese Patent No. 8-99999 discloses the use of PEG precipitation in combination with an SP-cation exchanger. The methods described therein do not separate fully active API from inactive API. The specific activity of fully active API should be 1.88 (using an Extinction coefficient 5.3), but the product achieved by this process only shows a relative activity of 1.0. Moreover, the best yield achieved by combining PEG precipitation and SP-cation exchange steps was only 50%, and does not appear to be easily scaled up to a commercial production level.

U.S. Pat. No. 5,610,285 discloses a purification process which combines successive anion and cation exchange chromatography steps. The initial anion exchange chromatography step binds API to the column; however, it also binds numerous contaminating proteins, particularly lipoproteins. Lipoproteins are plentiful in many of the materials from which API is isolated (e.g. Cohn IV-1 paste), and so tend to occlude the column. Such occlusion requires columns of considerable size, additional dialysis/filtration steps, and at least two cation chromatography steps. Those requirements reduce efficiency and practicality of the method for large-scale processes. Further, in the '285 process all API, both inactive and active protein, bind to the anion exchange column. When the API is eluted from that column in accordance with that method, i.e., high salt phosphate buffer, both active and inactive protein come off the column. Thus, there is no separation of the active from the inactive protein.

U.S. Pat. No. 6,093,804 discloses a method combining removal of lipoproteins from the source material, followed by subsequent anion and cation exchange steps, which result in highly purified, highly active API. However, this method proved to be efficient for small to mid-scale production of processing source material in the range of few kilograms.

As mentioned above, the demand for API exceeds available supply. Thus, there is a great need for, and it would be highly advantageous to have a process for a large-scale production of API, in which quality, which refers to both purity and activity, is not compromised for quantity. Moreover, it would be highly beneficial to have stable, viral-inactivated ready to use formulations of the purified API.

SUMMARY OF THE INVENTION

The present invention relates to a process for the production of alpha-1 proteinase inhibitor (API), suitable for processing scaled-up amounts of source material in the range of at least tens of kilograms, and which yields a highly purified, highly active API. The present invention also relates to formulations comprising the purified API, specifically to liquid formulations in which the API is highly stable and methods of using same.

The process provided by the present invention combines removal of contaminating substances (i.e., lipids, lipoproteins and other proteins) and separation of active from inactive API by sequential chromatography steps. The present invention discloses for the first time a process which is suitable for a large-scale production of API, i.e. for processing of source material amounts in the range of tens of kilograms. When the obtained source material is of high quality, i.e. the source material is obtained after filtration, the process of the present invention is suitable for processing source material amounts in the range of hundred of kilograms. Hitherto, processes described to yield API at high purity and activity were proved to be effective only for processing small to mid scale amounts of source material. As disclosed in the present invention, efficient large-scale API production is achieved by employing a combination of two methods for the removal of contaminating substances from an initial protein suspension, by the use of successive anion, cation and anion exchange resins with specific eluants and by meeting the GMP requirements of a large-scale production. In particular the methods of the present invention employ a minimum number of different buffers; automated preparation of solutions; use of solutions which can be kept under ambient storage conditions; and in particular avoid buffers and reagents prone to microbial contaminations. The purified API according to the present invention is at least 90%, preferably at least 95% pure (i.e. 95% w/w of the total protein) and of the purified API at least 90% is active. The yield of the disclosed large-scale process is preferably at least 50% from Cohn IV-1 paste, and typically at least 60%.

According to certain embodiments the end product of the process of the present invention is a liquid suitable for direct use. This currently preferred embodiment is advantageous to the currently available end product in the form of a powder, as, unlike powder, the liquid preparation requires no additional drying and subsequent reconstitution steps prior to administration. Furthermore, the API of the present invention is highly stable, and its formulations, including the liquid formulation, do not require any stabilizers.

According to one aspect, the present invention provides a process for the production of highly purified, active API. According to one embodiment, the end product of the process is in a liquid form.

According to one embodiment, the present invention provides a process for purifying alpha-1 proteinase inhibitor (API) from an unpurified mixture of proteins comprising:

a. dispersing the unpurified mixture of proteins containing API in an aqueous medium;
b. removing a portion of contaminating lipids and proteins by adding a lipid removal agent to the aqueous dispersion and precipitating the portion of contaminating proteins from said aqueous dispersion;
c. loading the API-containing supernatant of step (b) on a first anion exchange resin with a buffer solution having pH and conductivity such that API is retained on the first anion exchange resin;
d. eluting an API-containing fraction from said first anion exchange resin with the same type of buffer as in step (c) having adjusted pH and conductivity;
e. loading the API-containing fraction of step (d) on a cation exchange resin in said same type of buffer having appropriate pH and conductivity such that API is not retained on the cation exchange resin;
f. collecting the flow-through of step (e) that contains API;
g. loading the API-containing fraction of step (f) on a second anion exchange resin with said same type of buffer having appropriate pH and conductivity such that API binds to the second anion exchange resin;
h. eluting API from said second anion exchange resin with said same type of buffer having adjusted pH and conductivity to obtain a solution containing purified, active API.

According to one embodiment, the process of the present invention provides purified API comprising at least 60%, preferably at least 80%, more preferably at least 90% and most preferably at least 95% API out of the total protein, wherein at least 90%, preferably 95% of the pure API is active.

Throughout the process of the present invention only one type of buffer is used, with adjustment of pH and conductivity as required throughout the various process steps. As used herein, the term “one type” “same type” or “single type” of buffer, used herein interchangeably, refers to a buffer with one specific anion species.

According to one embodiment, the buffer is any suitable acid/salt combination that provides acceptable buffer capacity in ranges of pH required throughout the process of the present invention. According to preferred embodiments the process uses a buffer other than citrate-based buffer. According to yet another embodiment, the buffer anion is acetate. According to a further embodiment, the buffer solution is sodium acetate.

According to one embodiment, the process of the present invention further comprises viral removal and/or viral inactivation steps. Methods for viral removal and inactivation are known in the art.

One method for viral removal is filtration, preferably nanofiltration, removing both enveloped and non-enveloped viruses. According to one embodiment, the viral removal step comprises filtration. According to another embodiment, the virus removal step is performed after the cation exchange chromatography. Typically, the cation exchange flow-through solution containing API is concentrated, and then nanofiltered.

According to one embodiment, the method of viral inactivation employed by the present invention comprises a solvent/detergent (S/D) treatment. The viral inactivation step is preferably performed prior to loading the solution on the second anion exchange resin. According to one embodiment, the detergent used is polysorbate and the solvent is Tri-n-Butyl-Phosphate (TnBP). According to another embodiment, the polysorbate is polysorbate 80. According to one embodiment Polysorbate 80 may be added at from about 0.8% to about 1.3% volume per weight (v/w) of the resulting mixture and TnBP may be added from about 0.2% to about 0.4% weight per weight of the resulting mixture.

Any unpurified mixture of proteins containing a substantial amount of API may be used as a starting material for API purification according to the process of the present invention. According to one embodiment, the API-containing protein mixture is selected from plasma, particularly from plasma Cohn fractions IV paste. According to another embodiment, the API-containing protein mixture is Cohn fraction IV-I paste.

According to some embodiments of the present invention the unpurified mixture of proteins comprising API is dispersed in water, and the pH of the dispersion is adjusted to a pH range of from about 8.0 to about 9.5. The pH adjustment stabilizes the API and promotes the dissolution of the API in the dispersion, thereby increasing the production yield.

According to one embodiment, the lipid removal agent utilized for the removal of lipids and lipoproteins from the unpurified protein suspension is silicon dioxide (Aerosil™), and the contaminating proteins are precipitated from the suspension with polyalkylene glycol. According to one embodiment, the polyalkylene glycol is polyethylene glycol. According to yet another embodiment, the pH of the dispersion is reduced before the addition of the polyalkylene glycol. According to one currently preferred embodiment, the pH is reduced to a pH range of from about 5.0 to about 6.5. The pH reduction improves the precipitation, and the lipid removal agents and the precipitate are removed from the suspension. Removal of the precipitate from the solution can be performed by various methods as is known to a person skilled in the art, including centrifugation and filtration, specifically filter-press filtration. The supernatant from this step is in a pH range suitable for the first anion exchange chromatography (pH from about 5.0 to about 6.5). To further prepare the supernatant for loading on the anion exchange resin its conductivity is adjusted to from about 0.5 to about 3.5 mS/cm.

According to certain embodiments the first and the second anion exchange resin is a DEAE-Sepharose resin and the cation exchange resin is Carboxymethyl-Sepharose resin. The chromatography sequential steps according to the process of the present invention are performed with a single type of buffer throughout the process. However, individual sequential steps are performed under different pH and conductivity conditions, to provide the appropriate conditions required in each of those steps. The adjustment of the pH and conductivity in the buffer can be performed by any suitable method as is known to a person skilled in the art.

It has been previously shown that the separation of active from inactive API can be achieved by anion exchange chromatography. The cation exchange resin is used to further purify the API-containing fraction from substances that bind to the cation exchange resin, while the API passes through the resin. According to one embodiment, the pH of the API-containing fraction is adjusted to between 5.3 and 5.6 and the conductivity to from about 0.8 to about 1.1 mS/cm before loading the API-containing fraction on the cation exchange resin.

The present invention further comprises methods for separating active API from other contaminating substances, including solvent/detergent compounds used for viral inactivation as described herein above. According to one embodiment, this separation is advantageously achieved by the second anion exchange chromatography. According to one embodiment, before loading on the second anion exchange resin the pH of the API-containing fraction is adjusted to from about 6.0 to about 8.0 and the conductivity to from about 2.0 to about 4.0 mS/cm.

According to another embodiment, the process of the present invention further comprises the steps of changing the ionic composition of the solution containing purified, active API to contain a physiologically compatible ion and sterilizing the resulted solution to produce a fluid pharmaceutical preparation.

According to one embodiment, the solution containing the purified active API is concentrated before the ion exchange. According to another embodiment, the physiologically compatible ion is selected from the group consisting of phosphate ion, chloride ion and combinations thereof. Typically, the pH of the pharmaceutical preparation is about 7.0. According to yet another embodiment, the protein concentration of the solution containing the purified active API is adjusted to the range of 20-40 mg/ml prior to sterilization.

According to another aspect, the present invention provides a pharmaceutical preparation comprising a purified active API produced by the process of the present invention. According to yet another aspect, the present invention provides a pharmaceutical preparation comprising purified, active API in the form of ready to use sterile solution. This solution may be used for therapeutic, diagnostic or reagent purposes.

According to one embodiment, the fluid pharmaceutical preparation comprises at least 90%, preferably 95%, more preferably 99% API out of the total proteins. According to another embodiment, at least 90% of the API is in its active form. Typically, the pharmaceutical preparation contains from about 1% to about 3% API, preferably about 2% API.

According to one embodiment, the fluid pharmaceutical preparation is devoid of a stabilizing agent.

As used herein, the term "stabilizing agent" refers to a compound that stabilizes the active ingredient (herein API) within the pharmaceutical preparation. "Stabilization" refers to the process of preventing the loss of specific activity and/or changes in secondary structure from the native glycoproteins. Typically, such stabilizers include albumin, sucrose and mannitol.

According to one embodiment, the API in the fluid pharmaceutical preparation is stable for at least 3 month, preferably 4 month, more preferably 6 month when the pharmaceutical preparation is stored in a temperature range of between 20° C. to 25° C.

According to another embodiment, the API in the fluid pharmaceutical preparation is stable for at least 12 month, preferably 24 month, more preferably 36 month, when the pharmaceutical preparation is stored in a temperature range of between 2° C. to 8° C.

As used herein, the term "stable" refers to API activity at the end of the storage period that is at least 90%, preferably 95%, more preferably 100% the initial API activity.

According to yet another aspect, the present invention provides a pharmaceutical composition comprising as an active ingredient a therapeutically effective amount of API produced by the process of the present invention, further comprising a pharmaceutically acceptable excipient, diluent or carrier.

According to one embodiment, the pharmaceutical composition comprises at least 90%, preferably 95%, more preferably 99% API out of the total proteins. According to another embodiment, at least 90% of the API is in its active form.

Pharmaceutical compositions for use in accordance with the present invention may be formulated in conventional manner using one or more physiologically acceptable carriers, which facilitate processing of the active compounds into preparations which can be used pharmaceutically. Proper formulation is dependent upon the route of administration chosen.

According to one embodiment, the API produced by the process of the present invention is formulated in the form selected from the group consisting of aqueous solution and a powder. According to another embodiment, the pharmaceutical composition is devoid of a stabilizer.

For injection, the compounds of the invention may be formulated in aqueous solutions, preferably in physiologically compatible buffers such as Hank's solution, Ringer's solution, or physiological saline buffer.

For administration by inhalation, the fluid API produced according to the process of the present invention is conveniently delivered in the form of an aerosol spray, from a pressurized pack or a nebulizer. Aerosol spray is typically prepared with suitable propellant, e.g., dichlorodifluoromethane, trichlorofluoromethane, dichloro-tetrafluoroethane or carbon dioxide. In the case of a pressurized aerosol, the dosage unit may be determined by providing an apparatus comprising a valve to deliver a metered amount. Alternatively, lyophilized powder form of API produced by the process of the present invention can be mixed with a suitable powder base such as lactose or starch to form capsules and cartridges of, for example, gelatin for use in an inhaler or insufflator.

According to one currently preferred embodiment, the fluid pharmaceutical preparation is used to form an aerosol spray for inhalation.

According to yet another aspect, the present invention provides a method for treating a subject in need thereof comprising administering a therapeutically effective amount of API produced according to the process of the present invention.

According to one embodiment, the method is used for treating a disease or disorder selected from the group consisting of pulmonary emphysema, chronic obstructive pulmonary disorder, cystic fibrosis associated lung diseases and disorders, psoriasis and atopic dermatitis.

According to one embodiment the method is used for treating pulmonary emphysema.

According to another embodiment, the method is used for treating cystic fibrosis associated lung diseases and disorders.

According to one embodiment, the therapeutically effective amount of API is administered intravenously or by inhalation.

The present invention is explained in greater details in the description, figures, and claims below.

BRIEF DESCRIPTION OF THE FIGURES

FIG. 1 describes the protein profile on a native Tris-Glycine gradient gel during the API production process.

FIG. 2 describes the protein profile on a 4%-12% gradient SDS-PAGE during the API production process.

DETAILED DESCRIPTION OF THE INVENTION

Figure 1A:
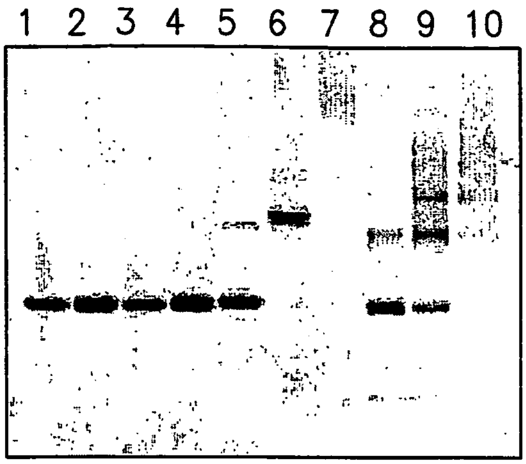
FIG. 1A: Coomassie blue stained gel.

The present invention provides a process for the production of highly pure, active and stable alpha-1 proteinase inhibitor (API) on a large-scale production. A particular advantage of the process provided by the present invention is its efficacy in processing source material in the range of tens to hundreds of kilograms, without compromising purity and activity of the API product, being at least 90% pure, of which at least 90% is active. The amount of source material that can be proceed according to the teaching of the present invention depended on the quality of the source material (higher amounts can be processed when the material is filtered). Furthermore, by the process of the present invention a ready to use liquid product could be obtained, comprising highly stable API.

Definitions

As used herein, the term "Alpha-1 proteinase inhibitor" (API) refers to a glycoprotein produced by the liver and secreted into the circulatory system. API belongs to the Serine Proteinase Inhibitor (Serpin) family of proteolytic inhibitors. This glycoprotein of MW of 50,600 Da consists of a single polypeptide chain containing one cysteine residue and 12-13% carbohydrates of the total molecular weight. API has three N-glycosylation sites at asparagine residues 46, 83 and 247, which are occupied by mixtures of complex bi- and triantennary glycans. This gives rise to multiple API isoforms, having isoelectric point in the range of 4.0 to 5.0. The glycan monosaccharides include N-acetylglucosamine, mannose, galactose, fucose and sialic acid. API serves as a pseudo-substrate for elastase; elastase attacks the reactive center loop of the API molecule by cleaving the bond between methionine$_{358}$-serine$_{359}$ residues to form an API-elastase complex. This complex is rapidly removed from the blood circulation. API is also referred to as "alpha-1 antitrypsin" (AAT). The term "glycoprotein" as used herein refers to a protein or peptide covalently linked to a carbohydrate. The carbohydrate may be monomeric or composed of oligosaccharides.

The term "cystic fibrosis" refers to an inherited autosomal recessive disorder caused by mutations in the gene encoding the cystic fibrosis transmembrane conductance regulator (CFTR) $Cl^-$ channel.

The term "Emphysema" refers to a condition in which there is a decrease in respiratory function and often breathlessness due to over-inflation of the alveoli in the lungs resulting from the damage done to the walls of the alveoli by the destructive neutrophil elastase.

As used herein, the term "API-containing pharmaceutical preparation" or "fluid pharmaceutical preparation" refers to the solution composition containing the purified API as obtained at the end of the process of the present invention. The term "pharmaceutical composition" refers to the aforementioned pharmaceutical preparation, further comprising excipients, diluents or carriers. The "pharmaceutical preparation" according to the present invention is always in the form of a liquid; the pharmaceutical composition may be in any suitable administering form, as is known in the art.

According to one embodiment, the present invention provides a process for purifying API from an unpurified mixture of proteins comprising:

a. dispersing the unpurified mixture of proteins containing API in an aqueous medium;
b. removing a portion of contaminating lipids and proteins by adding a lipid removal agent to the aqueous dispersion and precipitating the portion of contaminating proteins from said aqueous dispersion;
c. loading the API-containing supernatant of step (b) containing API on a first anion exchange resin with a buffer solution having pH and conductivity such that API is retained on the first anion exchange resin;
d. eluting an API-containing fraction from said first anion exchange resin with the same type of buffer as in step (c) having adjusted pH and conductivity;
e. loading the API-containing fraction of step (d) on a cation exchange resin in said same type of buffer having appropriate pH and conductivity such that API is not retained on the cation exchange resin;
f. collecting the flow-through of step (e) that contains API;
g. loading the API-containing fraction of step (f) on a second anion exchange resin with said same type of buffer having appropriate pH and conductivity such that API binds to the second anion exchange resin;
h. eluting API from said second anion exchange resin with said same type of buffer having adjusted pH and conductivity to obtain a solution containing purified, active API.

This process provides API fractions of at least about 90% API out of the total protein; often providing fractions of greater than about 95% pure API; and can achieve fractions of 99% pure API. Of the API, at least 90% is active. At least 95% active API is also achieved. Activity of API is measured by trypsin inhibition as exemplified herein below.

It has been previously disclosed that anion exchange chromatography is the principle stage in which active API is separated from inactive API, (U.S. Pat. No. 6,093,804). However, the method described in said US patent, adjusted to a small to mini-scale production, utilizes various buffer types to achieve such separation (loading the anion exchange with non-citrate buffer and eluting an API-containing fraction with citrate-based buffer). The present invention provides a process which meets the requirements of large-scale production, one of them being the use of minimal number of different solutions. The present invention therefore discloses the use of one type buffer in all chromatography steps, while adjusting the pH and conductivity of the buffer as required throughout the various process steps.

According to one embodiment, the buffer is any suitable acid/salt combination that provides acceptable buffer capacity in ranges of pH required throughout the process of the present invention. According to preferred embodiments the process uses a buffer other than citrate-based buffer. According to one embodiment, the anion buffer is acetate. According to another embodiment, the buffer solution is sodium acetate.

The sterility of the preparations of the present invention is of major concern, as the product should be administered to humans for therapeutic purposes, in particular by intravenous administration or by inhalation. Although the plasma source material is examined for the presence of contaminating viruses, and a great effort is taken to exclude contaminated donor fractions, there is a need to further assure that the end product of the process would be virus-free.

According to one embodiment, the process of the present invention further comprises viral removal and/or viral inactivation steps. Viral reduction can be accomplished by several processes, including nanofiltration; solvent/detergent treatment; iodine inactivation, e.g., treatment with an iodinated ion exchange matrix material such as iodinated SEPHADEX™ (as disclosed in PCT applications WO 97/48422 and WO 97/48482); treatment with Pathogen Inactivating Compounds; heat inactivation; gamma irradiation; or any other suitable virucidal process.

Lipid coated viruses are effectively inactivated by treatment with non-ionic biocompatible solvents and detergents. Methods for virus inactivation by solvent-detergent applications are described, for example, in EP 0131740. However, non-lipid coated viruses cannot be inactivated by solvent-detergent treatments, thus, other inactivation methodologies have to be used for their inactivation, including eliminating by physical means, e.g., the filtration of the preparation through very small filter holes so as to remove viruses by size exclusion (nanofiltration).

According to one embodiment, the viral removal step comprises filtration. Both enveloped and non-enveloped viruses are removed by filtration, preferably by nanofiltration, or any other filtration methods known in the art. According to one embodiment, a virus removal step is performed after the cation exchange chromatography. According to one embodiment, the cation exchange flow-through solution containing API may be concentrated by ultrafiltration. Prior to nanofiltration, the pH of the concentrated retentate may be adjusted to from about 6.8 to about 7.7, and its conductivity to from about 2.5 to about 3.5 mS/cm. The filtrate ("nanofiltrate") is collected for the subsequent step of viral inactivation.

According to one embodiment, the method of viral inactivation employed by the present invention comprises a solvent/detergent (S/D) treatment. This step is preferably taken prior to loading the solution on the second anion exchange resin. According to one embodiment, the detergent used is a non-ionic detergent such as polysorbate and the solvent is TnBP. According to another embodiment, the polysorbate is polysorbate 80. According to one embodiment Polysorbate 80 may be added at from about 0.8% to about 1.3% weight per weight of the resulting mixture and TnBP from about 0.2% to about 0.4% weight per weight of the resulting mixture. According to one embodiment, S/D viral inactivation is performed in a pH range of between about 6.0 and 9.0 and conductivity range of between about 2.0 and 4.0 mS/cm.

The unpurified mixture of proteins from which the API is collected is preferably Cohn Fraction IV-1 paste, but can include other Cohn Fractions, separately or in combination, human blood plasma, plasma fractions, or any protein preparation containing API. For instance, the present process is applicable to purification of recombinant human API from the milk of transgenic animals. (When milk may be used as starting material, an ammonium sulfate or sodium chloride precipitation step is first employed to separate API from caseins, and the precipitate is taken through the present purification process.) According to one embodiment, the unpurified mixture of proteins comprising API is dispersed in an aqueous medium, preferably water, at a ratio of between about 20 to about 35 liter per about 1 kg of source material, specifically Cohn Fraction IV-1 paste. The pH of the dispersion is adjusted to a pH range of from about 8.0 to about 9.5. The pH adjustment stabilizes the API and promotes the dissolution of the API in the dispersion, thereby increasing the production yield. Dispersion may take place at elevated temperature, for further increase in API solubility. According to one embodiment, dispersion is performed, or the solution is heated at a temperature of between 35° C. and 40° C.

A particular advantage of the present invention is the ready elimination of contaminants or by-products that otherwise compromise the efficiency of API purification processes. In particular, Cohn Fraction IV-1 paste preparations contain a significant amount of the lipoprotein Apo A-1, which has the effect of inhibiting column flow and capacity during purification. Other non-desired proteins such as albumin and transferrin are also present in the paste preparation. Removing a portion of such contaminants is performed according to the present invention by two sequential steps: (a) removing contaminating lipids and lipoproteins by lipid removal agent and (b) precipitating a portion of contaminating protein from the API-containing aqueous dispersion.

According to one embodiment, the lipid removal agent is silicon dioxide (Aerosil™). The Aerosil™ is added at a ratio of 1:10 to 1:14 Aerosil™: Kg of IV-1 paste. This step is performed at a high pH of about 9.0, and the resulting mixture is stirred for about 60-120 min. at a temperature of between 35° C. and 40° C. According to one embodiment, polyalkylene glycol is used for precipitating the portion of contaminating proteins, for example polyethylene glycol (PEG) or polypropylene glycol (PPG). Other alcohols known to those skilled in the art to have similar properties may be used. According to one embodiment, polyethylene glycol is used. According to yet another embodiment, the PEG used in the process of the present invention has a molecular weight of between 2,000 and 10,000 KDa, preferably has a molecular weight of between 3,500 and 4,500 KDa. The PEG added to the solution is at least about 2% weight per volume of the mixture formed. According to one embodiment, the PEG added is about 3% to 15% weight per volume of the mixture formed. According to another embodiment, PEG is added at between 10 to 12% weight per volume of the resulting mixture. Before the addition of the polyalkylene glycol the temperature of the mixture is adjusted to room temperature (at the range of from about 20° C. to 25° C.) and the pH of the dispersion is reduced. The pH reduction improves the precipitation and the supernatant from this step is in a pH range suitable for the first anion exchange chromatography. According to one embodiment, the pH is reduced to a pH range from about 5.0 to about 6.5 by the addition of, for example, acetic acid. In addition, a salt such as sodium chloride or the like may be added to the aqueous mixture in an amount sufficient to achieve a conductivity of from about 0.5 to about 3.5, to further prepare the supernatant for loading on the anion exchange resin. The removal of contaminating proteins, without loss of API, enables a significant reduction in equipment scale, e.g., column size.

All the above-described steps for removing contaminating substances are performed in one container, which is highly advantageous for a commercial, large-scale production process.

The precipitate that forms can be separated by conventional means such as centrifugation or filtration, and is then discarded. The supernatant is ready for further purification as described herein below. The above-described supernatant is loaded on an anion exchange resin. Various types of anion exchange resins can be used, including DEAE-Sephadex, QAE-Sephadex, DEAE-Sephacel, DEAE-cellulose, DEAE-Sepharose and the like. According to one embodiment, the anion exchange resin is DEAE-Sepharose. Variety of conditions may be used in this particular step. For best results the anion exchange medium is placed in a chromatographic column and the API eluted therefrom. According to one embodiment, the anion exchange resin is first equilibrated with step-wise buffer application, starting with a solution having a pH of about 3.5-4.5 and a conductivity of from about 8.0 to 12.0 mS/cm, and then with a solution of pH about 5.5-6.5 and a conductivity of from about 2.5 to about 3.5 mS/cm. After the resin is equilibrated, the above-described supernatant is loaded on the first anion exchange resin. These conditions of pH and conductivity allow the retention of API on the column, while the anion exchange medium is washed. The conductivity of the washing buffer (at a pH of about 5.5-6.5) is increased from about 1.8-2.4 to about 2.5-5.0 during the washing. This increase provides suitable conditions such that the column is loaded to its full capacity, and yet no API is discarded in the flowthrough, to give maximal API yield.

The API is then eluted from the column. According to one embodiment, elution is performed with a buffer solution having a pH of about 5.5 to 6.5 and conductivity of from about 9.0 to about 11 mS/cm.

Following separation of a solution containing API from an ion exchange resin, the solution is treated to reduce its water content and change the ionic composition by conventional means such as by diafiltration, ultrafiltration, lyophilization, etc., or combinations thereof.

According to one embodiment, the API-containing effluent obtained after the first anion exchange chromatography is concentrated by ultrafiltration. The retentate is then diafiltered against pure water to reach conductivity within the range of from about 3.5 to about 4.5 mS/cm.

To further purify the API-containing solution obtained after the first anion exchange chromatography the solution is loaded on a cation exchange resin with the same type of buffer used for the anion-exchange step, having appropriate pH and conductivity such to allow the API to pass and be washed off with the buffer flow through, while contaminating substances are retained on the cation exchange resin.

According to one embodiment, the cation exchange resin is carboxymethyl-sepharose resin, placed in a chromatography column. The cation exchange resin is first equilibrated with step—wise buffer applications, starting with a solution of pH about 3.5-4.5 and a conductivity of from about 8.0 to 12.0 mS/cm, and then with a solution of pH about 5.5-6.5 and a conductivity of from about 0.8 to about 1.1 mS/cm. The API-containing fraction is loaded on the column with the same buffer as in the second equilibration step (pH about 5.5-6.5 and a conductivity of from about 0.8 to about 1.1 mS/cm) and the flow through is collected.

Again, as disclosed herein above, the API-containing solution obtained after the cation exchange chromatography can be treated to reduce its water content. According to one embodiment, the solution is concentrated by ultrafiltration.

As disclosed herein above, the anion-exchange chromatography is used principally to separate active API from inactive API. The present invention further comprises methods for separating active API from other contaminating substances, including solvent/detergent compounds used for viral inactivation as described herein above.

According to one embodiment, such separation is achieved by the second anion exchange chromatography. The present invention shows that advantageously, contaminating substances, particularly non-ionic detergents and solvents commonly used for viral inactivation, are not retained in the DEAE-Sepharose anion exchange resin under the conditions of the present invention as detailed herein below. The API eluted from the second anion exchange chromatography step is therefore not only highly active, but also highly pure. The anion exchange resin is first equilibrated with step-wise buffer application, starting with a solution of pH about 3.5-4.5 and a conductivity of from about 8.0 to 12.0 mS/cm, and then with a solution of pH about 5.5-6.5 and a conductivity of from about 2.5 to about 3.5 mS/cm. Next, the API-containing fraction, typically, after viral inactivation treatment, is loaded on the second anion exchange resin. At this stage, the pH of the loading buffer may be elevated, and washing can be performed in one step, as the solution is already purified from the majority of contaminating proteins. According to one embodiment, the pH of the loading buffer is from about 6.0 to about 8.0 and the conductivity from about 2.0 to about 4.0 mS/cm. The pH of the washing buffer is about 5.5-6.5, and the conductivity about 2.5-3.5 mS/cm.

The API is then eluted from the column. According to one embodiment, elution is performed with a buffer solution at a pH of about 5.5 to 6.5 and conductivity of from about 11 to about 13 mS/cm.

The solution containing active, purified API obtained after the second anion exchange chromatography can be further processed to obtain pharmaceutical preparation for therapeutic, diagnostic, or other uses. To prepare the product for therapeutic administration the process of the present invention further comprises the steps of changing the ionic composition of the solution containing purified, active API to contain a physiologically compatible ion and sterilizing the resulted solution. Physiologically compatible substances used in the practice of the present invention are, for example, sodium chloride, sodium phosphate and glycine, having a buffered pH compatible with physiological conditions.

According to one embodiment, the ionic composition of the solution containing active, purified API is changed to contain the physiologically compatible phosphate ion by diafiltration against sodium phosphate buffer, at a physiological pH of about 7.0. The resulted solution is then concentrated and filter-sterilized to obtain a fluid pharmaceutical preparation suitable for therapeutic administration.

According to another aspect, the present invention provides a fluid pharmaceutical preparation comprising a purified active API produced by the process of the present invention. This solution may be used for therapeutic, diagnostic or reagent purposes.

According to one embodiment, the fluid pharmaceutical preparation comprises at least 90%, preferably 95%, more preferably 99% API out of the total proteins. According to another embodiment, at least 90% of the API is in its active form.

The API-containing pharmaceutical preparation of the present invention is highly pure. Compared to other plasma-derived approved products, the API-solution obtained by the methods of the present invention contains reduced amount of impurities. Hitherto known compositions of API include at least one protein stabilizer, including albumin, sucrose and mannitol. The present invention now discloses an API preparation which is devoid of a protein stabilizer, and yet is very stable, as exemplified herein below. This purity enables prescribing the API pharmaceutical preparation of the present invention to any subject in need thereof. For example, API preparation containing sucrose as a protein stabilizers are restricted from prescription to diabetes patients; mannitol is known to cause allergies to a certain percentage in the population, and thus administering mannitol-containing drug to a subject may cause anaphylactic reaction. Protein stabilizers, specifically protein stabilizers derived from human sources such as albumin are undesirable in the API-pharmaceutical preparation, as such proteins by themselves should undergo purification processes, and the final product may contain further impurities.

The purified API obtained by the process of the present invention is highly stable. According to one embodiment, the API in the fluid pharmaceutical preparation is stable for at least 3 month, preferably 4 month, more preferably 6 month when the pharmaceutical preparation is stored in a temperature range of between 20° C. to 25° C.

According to another embodiment, the API in the fluid pharmaceutical preparation is stable for at least 12 month, preferably 24 month, more preferably 36 month, when the pharmaceutical preparation is stored in a temperature range of between 2° C. to 8° C.

The filter-sterilized API-containing solution can be used directly, and also can be incorporated into pharmaceutical composition which may be used for therapeutic purposes. The term "pharmaceutical composition" is intended in a broader sense herein to include preparations containing a protein composition in accordance with this invention used not only for therapeutic purposes, but also for reagent or diagnostic purposes as known in the art or for tissue culture. The pharmaceutical composition intended for therapeutic use should contain a therapeutic amount of API, i.e., that amount necessary for preventative or curative health measures. If the pharmaceutical preparation is to be employed as a reagent or diagnostic, then it should contain reagent or diagnostic amounts of API.

According to yet another aspect, the present invention provides a pharmaceutical composition comprising as an active ingredient a therapeutically effective amount of API produced by the process of the present invention, further comprising a pharmaceutically acceptable excipient, diluent or carrier.

As used herein, the term "therapeutically effective amount" refers to an amount of a protein or protein formulation or composition which is effective to treat a condition in an living organism to whom it is administered over some period of time.

According to one embodiment, the pharmaceutical composition comprises at least 90%, preferably 95%, more preferably 99% API out of the total proteins. According to another embodiment, at least 90% of the API is in its active form.

Pharmaceutical compositions of the present invention may be manufactured by processes well known in the art, e.g. by means of conventional mixing, dissolving, granulating, grinding, pulverizing, dragee-making, levigating, emulsifying, encapsulating, entrapping or lyophilizing processes.

Pharmaceutical composition for use in accordance with the present invention thus may be formulated in conventional manner using one or more acceptable diluents or carriers comprising excipients and auxiliaries, which facilitate processing of the active compounds into preparations, which can be used pharmaceutically. Proper formulation is dependent on the route of administration chosen.

API formulations or compositions may be appropriate for a variety of modes of administration. These may include oral, parenteral, subcutaneous, intravenous, pulmonary, intralesional, or topical administration. According to certain embodiments, the present invention relates to pharmaceutical compositions to be administered parenterally and by inhalation.

Pharmaceutical compositions for parenteral administration may be formulated for intravenous injections, intravenous infusion, intradermal, intralesional, intramuscular, and subcutaneous injections or depots. The API-containing pharmaceutical preparation produced by the process of the present invention is advantageous over hitherto known API-containing preparation, as the API is highly stable also when the preparation is kept in a liquid from. Therefore, it is not necessary to lyophilize the API-preparation for stable storage in a form of a powder. Subsequently, there is no need to reinstate the powder to a liquid before use for parenteral administration.

As described herein above, API is used for the treatment of pulmonary diseases. Intravenous administered API affects such pulmonary diseases by diffusing into the lung and neutralizing elastase and other proteases. By examining broncho-alveolar lavage (BAL) specimens it has been shown that exogenous API, administered intravenously and diffused into the lungs caused an increase of more than 3-fold in the pulmonary API levels, and that the anti-elastase activity doubles 6 days after API infusion (Wewers et al., Am. Rev. Respir. Dis. 135:539-43, 1987). Nevertheless, when administered intravenously most of the API never reaches the lung. It has been estimated that only 2% of the intravenously administered dose reaches the lung (Hubbard & Crystal, Lung (Suppl): 565-578, 1990).

Therefore, administration of API by the inhalation route may be more beneficial as it reaches directly the lower respiratory tract. This route should require lower therapeutic doses of API and thus the scarce supply of human plasma-derived API would be available for the treatment of more patients. This rout of administration may be also more effective in neutralizing neutrophil elastase. In addition, administration by inhalation is simpler and less stressful for the patient than the intravenous route and would reduce the burden on the local health care system (by requiring less clinical input).

Formulations of pharmaceutical compositions for administration by the rout of inhalation are known in the art. In general, for administration by inhalation, the active ingredients are delivered in the form of an aerosol spray from a pressurized pack or a nebulizer with the use of a suitable propellant, e.g., dichlorodifluoromethane, trichlorofluoromethane, dichloro-tetrafluoroethane or carbon dioxide. The operating conditions for delivery of a suitable inhalation dose will vary according to the type of mechanical device employed. For some aerosol delivery systems, such as nebulizers, the frequency of administration and operating period will be dictated chiefly by the amount of the active composition (API according to the present invention) per unit volume in the aerosol. Typically, the higher the concentration of the protein in the nebulizer solution the shorter is the operating period. Some devices such as metered dose inhalers may produce higher aerosol concentrations than others and thus will be operated for shorter periods to give the desired result.

Other devices such as powder inhalers are designed to be used until a given charge of active material is exhausted from the device. The charge loaded into the device will be formulated accordingly to contain the proper inhalation dose amount of API for delivery in a single administration. (See generally, Remington's Pharmaceutical Sciences, 18th Ed. 1990, Mack Publishing Co., Easton, Pa., Chapter 92 for information relating to aerosol administration).

Regardless of what device is used for aerosolization, the active ingredient will be in the form of a dispersion of particles. The dispersion of particles may be in the form of liquid droplets or in the form of powder (dry or suspended). According to one embodiment, the API-containing fluid pharmaceutical preparation will be used directly for aerosolization.

According to yet another aspect, the present invention provides a method for treating a patient in need thereof comprising administering a therapeutically effective amount of API produced by the process of the present invention.

According to one embodiment, the method is used for treating pulmonary emphysema. It is known that patients with API deficiency have a low level burden of neutrophils in their lower respiratory tracts. Evaluation of the API levels and anti-neutrophil elastase defenses in such patients demonstrated that both are markedly reduced. Taken together, these observations support the hypothesis that a deficiency of API predisposes a patient to emphysema by altering the balance between neutrophil elastase and anti-neutrophil elastase in the lower respiratory tract. Whereas normal persons have an adequate anti-neutrophil elastase screen to protect the lower respiratory tract, those with API deficiency do not, permitting the neutrophil elastase to destroy lung tissue. Thus, providing patient with endogenous API-deficiency with exogenic API at the correct dose can overcome the deleterious effects of such deficiency.

According to another embodiment, the method is used for treating lung diseases and disorders associated with cystic fibrosis.

Loss of pulmonary function is a primary cause of death in patients suffering from cystic fibrosis. Patients with a Forced Expiratory Volume in one second (FEV1) below 30% of their predicted value have a 2-year mortality of greater than 50%. The current mortality rate is 1.2 deaths per 100 patients per year; the median survival is 32 years. Of the deaths in which a case was specified, 94% were due to cardiorespiratory failure. Respiratory failure is characterized by increasing dyspnea, hypoxemia and elevation of arterial $PCO_2$. During their lifetime, CF patients are restricted in their day-to-day activities due to reduced lung function and constant pulmonary infections as a result of their condition.

One of the major side effects of chronic infection associated with CF is the chronic presence of phagocytic neutrophils in the lungs in response to bacterial infections and the release of various chemoattractants. These leukocytes secrete elastase, which has the potential to destroy the elastic tissue of the lung. In addition, neutrophils of patients with CF have been shown to be in a state of increased responsiveness and tend to degranulate more readily, releasing tissue-destroying elastase. Thus, patients with CF appear to have a state of unregulated inflammatory response, which overwhelms the normal protease (elastase)/antiprotease (API) balance, leading to the accumulation of elastase in the lung and ultimately to tissue damage.

Previous studies have shown that much of the pulmonary damage in CF results from the presence of unneutralized elastase and other proteases. The abnormal cycle is destructively self-perpetuating and self-expanding: increased elastase leads to the recruitment of more neutrophils to the lung that in turn secrete additional proteases. This cycle further overwhelms the natural normal protease (elastase)/antiprotease balance leading to destruction of the lung architecture, severe pulmonary dysfunction and ultimately death.

Patients with CF suffer from chronic lung infections that have to be treated with antibiotics. For example, azithromycin, an antibiotic recently proven to be effective in the treatment of *Pseudomonas aeruginosa* bacteria. With the increased longevity of CF patients, there will be associated newer infections such as *B. cepacia* and *S. maltophilia*. It is possible that prophylactic use of API in CF patients may improve their pulmonary function and thereby reduce the occurrence of such infections.

Preferably, API is administered to CF patients by the inhalation route. It has been previously demonstrated (McElvaney et al, 1991) that aerosolized alpha-anti-trypsin given to cystic fibrosis patients suppressed neutrophil elastase in the respiratory epithelial lining fluid (ELF), restored the anti-neutrophil elastase capacity in the ELF and reversed the inhibitory effect of the ELF on the ability of neutrophils to effectively combat *Pseudomonas* infection. Advantageously, aerosol formulations can be readily produced using the API liquid preparation of the present invention. For aerosolized formulation, higher API concentration in the range of 10% is required. As exemplified herein below, API produced by the process of the present invention is essentially stable at this concentration for at least 8 weeks, preferably for 12 weeks, when stored at a temperature range of 2-8° C.

The principles of the invention, may be better understood with reference to the non-limiting examples below.

EXAMPLES

Measuring API Activity

Concentration of active API is determined by inhibition of porcine pancreatic elastase. In principle, the assay compares between the inhibition rate of elastase obtained with a test sample and the inhibition rate of elastase obtained with API a reference standard (Kamada, Israel), which is considered as having 100% activity. Elastase activity is measured by the rate of cleavage of the elastase substrate (Succinyl-Alanine-Alanine-Alanine-p-Nitroanilide) resulting in the release of the cleavage product, which absorbs at 405 nm. The decrease of elastase activity in the presence of API is in direct relation with the amount of active API in the reaction mixture.

Activity of API reference standard is estimated by inhibition of trypsin esterase activity. Active API binds active trypsin in a stoichiometric ratio of 1:1 under the assay conditions and decrease trypsin esterase activity, which is measured according to a method similar to the USP 25 method. The amount of trypsin active sites in the trypsin preparation is determined previously by titration with p-Nitrophenyl-p-Guanidino-Benzoate (NPGB): The increment of absorption at 402 nm of the trypsin preparation following addition of the titration substrate is in direct correlation with the amount of active trypsin molecules present in the trypsin preparation.

Example 1

Pretreatment of the Source Material

In a preferred embodiment, the starting material is Cohn Fraction IV-1 paste, which is obtained by the Cohn-Oncley fractionation technique, well known to those of skill in the art. The preparation of an aqueous solution from the Fraction IV-1 paste is described below.

The IV-1 paste is dissolved in about 35 volumes of water-for-injection grade water, (IV-1 paste weight in kg times 35). The amount of starting paste, 75-87 Kg per purification process, is added to a jacketed stainless steel tank in portion. The pH of the mixture is adjusted to 9.2 immediately after mixing of the first portion, and it was further adjusted by 0.5N NaOH until all the paste and water are added. The solution is mixed for approximately 10 minutes.

Fraction IV-I paste, like other plasma fractions, contains various proteins, such as lipoproteins, immunoglobulins, globulin, metalloproteins, etc. These proteins must be separated from the API to produce a liquid stable preparation, but some will also bind to an ion exchange resin and thereby interfere with the purification of API. Before adding the solution to an anion exchange resin, therefore, a portion of these contaminating proteins is preferably removed. According to the present invention, removing such contaminating fraction is performed by two steps.

Removing of Lipids and Lipoproteins

To the dispersion obtained above a lipid-removing agent, Aerosil™ (silicon dioxide) was added at 78-82 g/Kg paste. After the addition of Aerosil, the pH of the resulting mixture was adjusted to 8.8 with NaOH 0.5N. The mixture was incubated for 90 min. at 38° C. and a stirring rate of 870-1450 rpm. After 90 min. the dispersion was cooled to 22.5° C. and the pH was adjusted to 6.1.

Precipitation of Contaminating Proteins

To the cooled dispersion obtained as above Polyethylene glycol (PEG) of mean molecular weight of 4,000 KDa was added at 10.5-11.5% weight per volume of the resulted mixture while stirring at 2660-2900 rpm. After PEG dissolution the pH of the dispersion was adjusted to 6.0 with 2% acetic acid. Conductivity was adjusted with solid NaCl to 3.0 mS. A precipitate of contaminating proteins and viruses, including prion proteins, was formed. This precipitate was removed by continuous centrifugation (Self-desludging centrifuge, model CSA19-06-476, Westfalia) at a centrifugation rate of 300-450 liter/hr. The sediment obtained by the centrifugation was discarded; the supernatant was further filtered using 1 μm (nominal) cellulose fiber depth filter and a pressure of ≦25 psi.

Example 2

First Anion Exchange Chromatography

The resin used for the first anion exchange chromatography was DEAE-Sepharose fast Flow, packed in a stainless steel 316-L column (CF 1000/150 SS CHROMAFLOW, Pharmacia), having a volume of 117 liter.

The DEAE-Sepharose resin was first equilibrated stepwise with sodium acetate buffer as follows:

a) pH 4.0, conductivity 10.0 mS/cm b) pH 6.0, conductivity 3.0 mS/cm

Flow rate: 7-20 liter/min.

After the procedure described in example 1 the filtered supernatant obtained was already at the suitable pH and conductivity conditions of pH 6.0 and 3.0 mS/cm. It was therefore directly loaded on the equilibrated DEAE-Sepharose column, at a flow rate of 12-14 liter/min.

In such large-scale production, it is critical to adjust the washing conditions such that the column will be loaded at its maximal capacity, and yet that no API would leak out in the flow through. This was achieved by a two-step column wash, both with sodium acetate buffer at the following conditions: first wash—pH 6.0, conductivity 2.1 mS/cm; second wash: pH 6.0, conductivity 3.0 mS/cm. The API is retained on the column, and other proteins, for example albumin and transferrin are washed out.

Elution of the API from the column was performed with a sodium acetate buffer having a pH of 6.2 and conductivity of 10.0 mS/cm. The pressure on the column was ≦35 psi and the flow rate 12-14 liter/min. The API-containing fraction was then treated to adjust its water content and ion composition as described in Example 3 below.

Example 3

Adjustment of Water Content and Ion Composition

The API-containing effluent was concentrated to 100 kg (total weight) by ultrafiltration with polysulfone membrane with a nominal cut off of 10 kD and total membrane area of 12.2 $m^2$ (UFP-10C-65) in a Hollow Fiber cartridge (Amersham Biosciences). The retentate pressure was 15-20 psi and the flow rate 20-40 liter/min. The filtrate was then discarded and the retentate was diafiltered against water-for-injection (WFI) grade water. The retentate pressure was 15-20 psi at a flow rate of 20-40 liter/min., and the diafiltration was continued until the solution reached a conductivity of 4.0 mS/min.

Example 4

Cation Exchange Chromatography

To further purify the API-containing fraction obtained after the procedure of example 3 from remaining contaminating substance, the solution was subjected to cation exchange chromatography using the same sodium acetate buffer under conditions which allow the retention of only the contaminating substances of the cation resin, while the API was washed out with the column flow through.

The cation exchange resin used was CM-Sepharose Fast Flow, packed in a stainless steel 316-L column (CF 1000/150 SS CHROMAFLOW, Pharmacia), having a volume of 117 liter.

The resin was equilibrated with sodium acetate buffer under the following conditions:

a) pH 4.0, conductivity 10.0 mS/cm;

b) pH 5.35, conductivity 0.95 mS/cm

Flow rate: 7-22 liter/min.

Before loading the API-containing fraction on the column, the conductivity of the solution was adjusted with NaCl to 0.95 mS/cm and the pH was adjusted with 2% acetic acid to 5.35. The protein concentration of the solution was 0.5%, and total protein load was ≦4 Kg. Flow rate was 18-22 liter/min at a pressure of 29≦psi. The column flow through containing the API was collected. The pH was adjusted to 6.75 with 0.15 M NaOH and the conductivity to 3.0 mS/cm with solid NaCl. The resulting solution was ultrafiltered using polysulfone membrane with a nominal cut off of 10 Kd and total membrane area of 12.2 $m^2$ (UFP-10C-65) in a Hollow Fiber cartridge (Amersham Biosciences). The retentate was collected and the effluent discarded.

Example 5

Viral Inactivation

In a preferred embodiment of the invention, the API-containing fraction obtained after the action exchange chromatography is subjected to viral removal and inactivation.

According to the preferred embodiment, viral removal was performed by nanofiltration. The API-containing solution was subjected to pre-filtration through polysulfone membrane with a pore size of 0.1+0.2 μm, nominal surface area of 0.6 $m^2$ (5441358 K-1 SS, Sartorius), at a pressure of ≦30 psi. The retentate was collected in 600 liters stainless steel 316-L jacketed and pressurized container equipped with a marine type stirrer. The retentate was diluted with WFI to protein concentration of 6.0-8.5 mg/ml, and pH and conductivity was re-adjusted to 7.25 with 0.15 M NaOH/2% acetic acid and 3.0 mS/cm with solid NaCl, respectively. The temperature of the container was kept at 22.5° C.

Nanofiltration was performed with Planova 15N filter (15N1-000; Asahi Kasei Corporation) having a nominal surface are of 1.0 $m^2$. The operating pressure obtained by $N_2$ was 13.8 psi. Volume transferred per $m^2$ of filter was more than 250 liters.

Further to virus removal, the API-containing solution was subjected to viral inactivation using the solvent/detergent method. Polysorbate 80 was added to 0.95-1.25% w/w final concentration and TnBP to a final concentration of 0.28-0.33% v/w. The mixture was stirred for about 4.5-5.5 hrs. at 30-50 rpm.

Example 6

Second Anion Exchange Chromatography

Second anion exchange chromatography is employed to further purify the API-containing solution obtained after viral inactivation from the employed solvent and detergent. As during the steps taken after the first anion exchange chromatography some of the active API may have become inactive, inactive AP is also removed. Thus, the resulting solution after this step contains highly purified, active API.

The resin used for the second anion exchange chromatography was DEAE-Sepharose Fast Flow, packed in a stainless steel 316-L column (BPSS 800/150 SS, Pharmacia), having a volume of 75 liter.

The DEAE-Sepharose resin was first equilibrated stepwise with sodium acetate buffer as follows:

a) pH 4.0, conductivity 10.0 mS/cm b) pH 6.0, conductivity 3.0 mS/cm

As the API-containing fraction was now partially purified, a faster flow rate of 18-22 liter/min. was employed. Of the same reason, the pH of this fraction could be elevated to 7.5 and the column could be washed with one set of buffer conditions. The conductivity of the loaded solution was 3.0 mS/cm, and the total protein load about 2.5 Kg. The pH of the sodium acetate washing buffer was 6.0 and its conductivity 3.0 mS/cm. Total wash volume was 1125-1200 liter at a flow rate of 18-22 liter/min.

Elution of the API from the column was performed with a sodium acetate buffer having a pH of 6.0 and conductivity of 12.0 mS/cm. The eluate of the second anion exchange column contained 96% pure API, of which more than 90% were active.

Example 7

Purity of API Through the Process

Figure 1B:
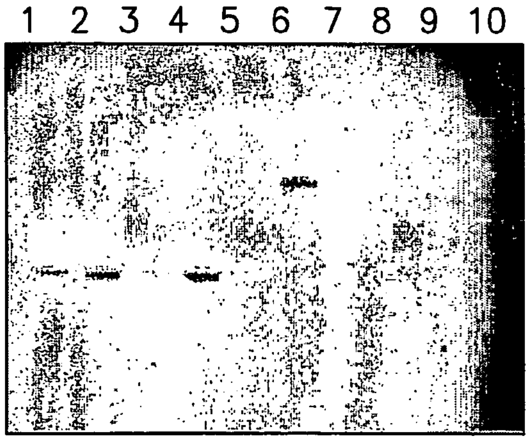
FIG. 1B: Ponceau-S stained gel.
Figure 1C:
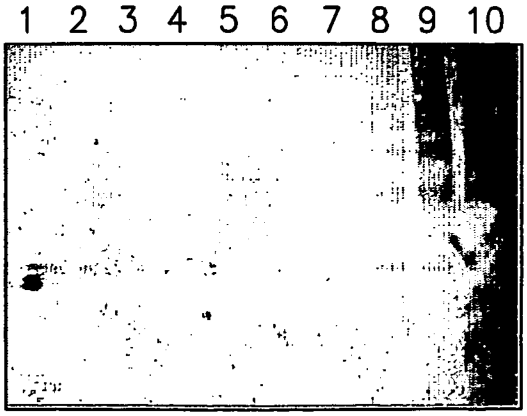
FIG. 1C: Immunoblot with Goat anti-API, HRP-conjugate antibodies. Lanes of the gels are as follows: 1,2—Final drug product; 3,4—In house API standard; 5—Albumin; 6—Transferrin; Anti-D (IgG); 8, 9, 10—Polymeric fraction of API.

Samples from different steps of the process were analyzed by techniques of protein separation and detection. FIG. 1 describes the protein profile of API in the pharmaceutical preparation produced by the process of the present invention; standard API prepared by Kamda, Israel; and polymeric API on native Tris-Glycine 8% to 16% gradient gels. Under native conditions, proteins are separated according to both, molecular weight and structure. Non-denatured samples were loaded in a sample buffer (Invitrogen™ LC2673) on the gels in the amounts detailed in table 1. Polymeric forms of API were derived from a purified API (lot No. 6110003, Kamada) stored at 35° C. for 6 months that was subjected to gel permeation chromatography using Sephacryl 200HR column. Three fractions (lanes 8-10) were collected for analysis on the native gels. The gels were run in a Tris-Glycine running buffer (10× Invitrogen™ LC2672). The gels were stained by Commassie blue (FIG. 1A), Ponceau-S (FIG. 1B) or blotted onto a nitrocellulose membrane (BioRad Trans Blot). Immunobloting was then performed using anti-human API antibodies, conjugated with horseradish peroxidase (HRP,ICN/Cappel, 55236), used at a dilution of 1:400 (FIG. 1C).

TABLE 1

Samples loaded onto the native gels

| Lane(s) | Sample | Protein loaded (μg/lane) A | B |
|---|---|---|---|
| 1/2 | Final drug product | 2.5/5 | 1/2 |
| 3/4 | In-house API standard | 2.5/5 | 1/2 |
| 5 | Albumin | 3.5 | 1.4 |
| 6 | Transferrin | 3.5 | 1.4 |
| 7 | Anti-D (IgG) | 3.5 | 1.4 |
| 8 | Polymeric fraction of API | 3.6 | 1.44 |
| 9 | Polymeric fraction of API | 3.6 | 1.49 |
| 10 | Polymeric fraction of API | 3.6 | 1.32 |

Figure 2A:
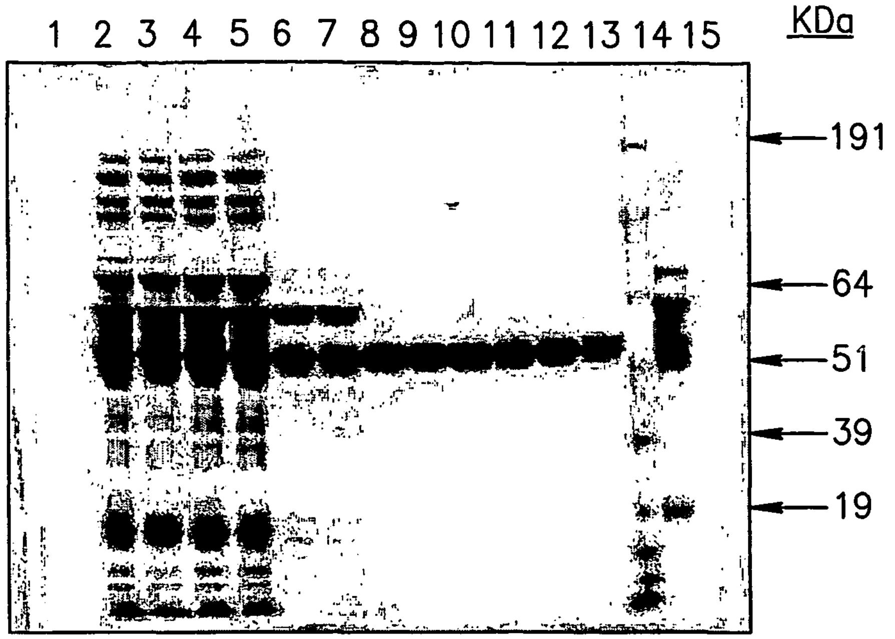
FIG. 2A: Coomassie blue stained gel.
Figure 2B:
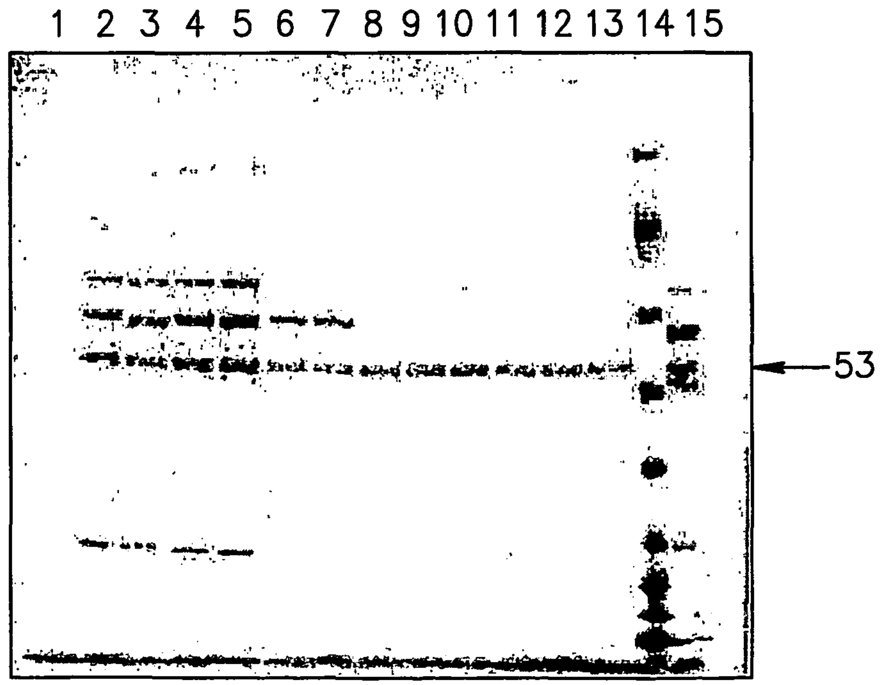
FIG. 2B: Ponceau-S stained gel.

Samples obtained during the purification process were separated by 4-12% SDS-PAGE. Gels were stained with Commassie Blue (FIG. 2A), Ponceau-S staining (FIG. 2B) or immunoblotted with Goat anti-API, HRP-conjugate antibodies. Samples are detailed in table 2.

TABLE 2

Samples loaded onto the SDS-PAGE gels

| Lane(s) | Sample | Protein loaded (μg/lane) A | B |
|---|---|---|---|
| 1 | Sample buffer | | |
| 2, 3 | Pre-Aerosil | 15 | 3 |
| 4, 5 | Pre-PEG | 15 | 3 |
| 6, 7 | First DEAE eluate | 4.0 | 0.8 |
| 8, 9 | Ultrafiltration after cation exchange | 2.0 | 0.4 |
| 10 | Second DEAE eluate | 2.0 | 0.4 |
| 11 | Drug substance | 2.0 | 0.4 |
| 12, 13 | Drug product | 2.0 | 0.4 |
| 14 | MW size marker - commercial | 10 μl per lane | |
| 15 | MW in-house marker | 4.6 | 2.3 |

Figure 2C:
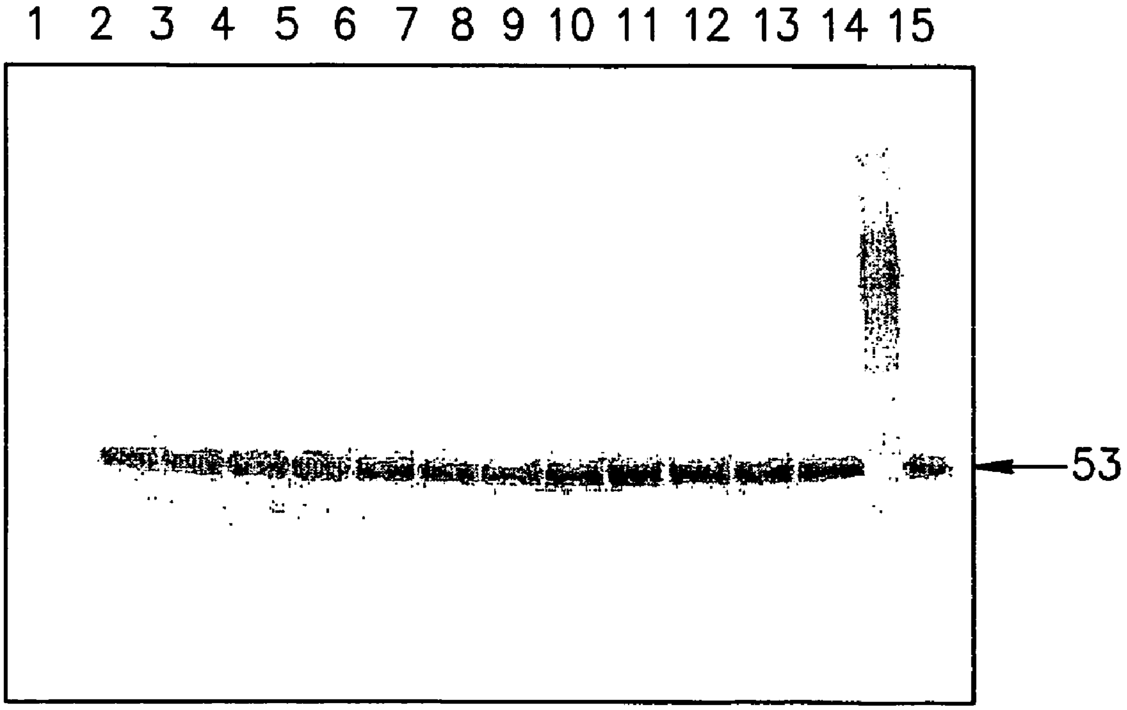
FIG. 2C: Immunoblot with Goat anti-API, HRP-conjugate antibodies. Lanes of the gels are as follows: 1—Sample buffer; 2,3—dispersion before the addition of Aerosil; 4, 5: Dispersion before the addition of PEG; 6,7: eluate after first anion exchange chromatography; 8, 9: filtrate after cation exchange chromatography; 10: eluate after second anion exchange chromatography; 11: end product of the process (drug substance); 12, 13: formulated API (drug product); 14, 15—commercial and in-house molecular weight standards, respectively.

FIGS. 1 and 2 clearly show that most contaminating proteins are removed during the process of the present invention. The final drug substance shows only one sharp and clean band.

Example 8

Further Purification of API

After the second anion exchange chromatography described in Example 6, the fraction containing the active, pure API was concentrated by ultrafiltration (UFP-10C-65: polysulfone membrane with nominal cut off of 10 KDa and total nominal membrane area of 12.2 $m^2$). The filtrate was discarded and the retentate, concentrated to 60 kg was further subjected to diafiltration. Diafiltration was performed to replace the acetate ion by physiologically acceptable ion, specifically phosphate ion. The diafiltration conditions were filtration against sodium phosphate buffer, 18-22 nM in 0.6-0.8% NaCl, pH 7.0, retentate pressure of 15-20 psi. Final pH of the retentate was a physiological pH of 7.0. After second ultrafiltration, the protein concentration was brought to 22-24 mg/ml. The preparation was filter sterilized using two polysulfone filters of 0.45 and 0.2 μm (Sartorius, 5101507H9-B) in a serial placement. Filtration was performed under a pressure of ≦25 psi and the sterile filtrate was collected in pre steam-sterilized container. The final API-containing preparation comprised 22-24 mg/ml protein at a pH of 7.0±0.1, NaCl at a concentration of 6-8 mg/ml and phosphate concentration of 18-22 mM. This solution is a pharmaceutical grade, ready to use preparation, and is therefore designated as pharmaceutical preparation.

Example 9

Characterization of Physico-Chemical and Structural Properties of API

Characterization studies of three lots of the API containing pharmaceutical preparation produced by the process of the present invention by the Kamada (Israel): were performed to obtain information on physico-chemical and structural properties of the API molecule. Three lts were examined: lots 6112006, 6113010 and 6123010. The analyses of lot #6112006 (manufacturing: June 2002) were performed after 12-20 months storage of the lot at 2-8° C., whereas the analyses of lots #6112010 and #6123010 (manufacturing: October 2003) were initiated immediately after the production and were completed within 3 months in which the lots were stored at 2-8° C.

The characterization studies were performed in three laboratories, at the Kamada Analytical R&D and Validation Laboratory (Israel), at M-Scan Limited (UK) and at the Weizmann Institute of Science (Israel).

Mass-Spectrometry of Intact Protein

Delayed Extraction-Matrix Assisted Laser Desorption Ionization-Time of Flight (MALDI-TOF MS) Mass Spectrometry was used for the determination of the intact molecular weight of API.

MALDI-TOF MS is a technique in which a co-precipitate of a UV-light absorbing matrix and a protein molecule are irradiated by a nanosecond laser pulse. Most of the laser energy is absorbed by the matrix, which prevents unwanted fragmentation of the molecule. The ionized protein molecules are accelerated in an electric field and enter the flight tube. During the flight in this tube different molecules are separated according to their mass to charge ratio and reach the detector at different times. In this way each molecule yields a distinct signal. This method allows accurate measurement of intact molecular weight of biopolymers from 400 up to 500,000 Da.

All the tree lots examined had a comparable intact molecular weight, as shown in Table 3 below:

TABLE 3

| Molecular weight of intact API | |
|---|---|
| API Lot # | Intact Molecular Weight, Da |
| 6112006 | 50,600 Da ± 50 Da |
| 6113010 | 50,550 Da ± 50 Da |
| 6123010 | 50,500 Da ± 50 Da |

Amino Acid Composition Analysis and Determination of the Extinction Coefficient

Amino acid composition is an important characteristic of proteins. The combination of the amino acid analysis with spectrophotometric determination of the absorbance at 280 nm allowed the determination of the molar extinction coefficient of API. Dividing the molar extinction coefficient of the protein by its intact molecular weight results in the extinction coefficient of a 0.1% protein solution.

For amino acid analysis, the API lot samples were hydrolysed with constant boiling HCl, derivatized using Phenylisothiocyanate and analyzed by Reverse Phase (RP)-HPLC. API in lots 6112006, 6113010 and 6123010 had comparable amino acid compositions (See Table 4 below). The slight differences in the content of aspartic and glutamic acids between API lot 6112006 and API lots 6113010 and 6123010 are related to the duration of hydrolysis; 24 h for lot 6112006 compared to 16 h for lots 6113010 and 6123010.

TABLE 4

| Amino Acid Composition | | | | |
|---|---|---|---|---|
| Amino acid | Expected ratio | API Lot #6112006, Calculated ratio relative to Leu = 45 | API Lot #6113010, Calculated ratio relative to Leu = 45 | API Lot #61213010, Calculated ratio relative to Leu = 45 |
| Aspartic acid | 43 | 28.5 | 16.9 | 16.0 |
| Glutamic acid | 50 | 42.5 | 27.4 | 26.1 |
| Serine | 21 | 19.9 | 20.2 | 20.9 |
| Glycine | 22 | 21.6 | 20.9 | 21.6 |
| Histidine | 13 | 13.9 | 12.9 | 12.9 |
| Arginine | 7 | 7.6 | 7.0 | 7.0 |
| Threonine | 30 | 25.5 | 29.5 | 28.7 |
| Alanine | 24 | 23.4 | 23.3 | 23.4 |
| Proline | 17 | 16.9 | 16.5 | 17.2 |
| Tyrosine | 6 | 5.7 | 5.8 | 5.8 |
| Valine | 24 | 21.8 | 21.7 | 21.3 |
| Methionine | 9 | 9.3 | 8.9 | 9.2 |
| Isoleucine | 19 | 17.4 | 17.0 | 16.7 |
| Leucine | 45 | 45.0 | 45.0 | 45.0 |
| Phenylalanine | 27 | 27.0 | 26.7 | 26.5 |
| Lysine | 34 | 35.5 | 30.7 | 30.2 |
| Tryptophan | 2 | ND | ND | ND |
| Cystein | 1 | ND | ND | ND |

ND = not detected

The extinction coefficient of API was measured for lot #6113010 and #6123010 which had comparable extinction coefficients, as is shown in Table 5.

TABLE 5

| API Extinction Coefficient | | |
|---|---|---|
| API Lot # | Molar Extinction Coefficient, $L \cdot mol^{-1} \cdot cm^{-1}$ | Extinction Coefficient (0.1%) at 280 nm |
| 6113010 | 24,618 | 0.49 |
| 6123010 | 22,908 | 0.45 |

Peptide Mapping

Peptide Mapping was performed following Cyanogen bromide (CNBr) digestion, using MALDI-MS and on-line LC-Electrospray (ES) MS. The concept of the chosen method of mapping is generation of peptides by chemical digestion, determination of their molecular weights and accurate determination of the presence or absence of the components parts of the known protein sequence. The techniques of ES-MS using an atmospheric pressure ionisation source and MALDI-MS create the possibility of accurately measuring the intact molecular weights of biopolymers up to 130 kDa and 500 kDa respectively. The coupling of on-line microbore and nano-capillary HPLC directly with Electrospray Mass Spectrometric detection of the separated digest products increases the power of the technique. A definite advantage of this mapping procedure is that there is an equal probability of observing the C-terminal as well as the N-terminal regions of the protein.

Peptide mapping profile of all three lot examined, lots #6112006, #6113010 and #6123010 is presented in Table 6, showing that all three lots have a comparable profile.

TABLE 6

| Peptide Mapping by Cyanogen Bromide (CNBr) Digestion | | | |
|---|---|---|---|
| Item | Lot #6112006, Molecular Mass of Peptide/ Glycopeptide | Lot #6113010, Molecular Mass of Peptide/ Glycopeptide | Lot #6123010, Molecular Mass of Peptide/ Glycopeptide |
| Glycopeptide 243-351 residue (homoserine) plus $NeuAc_2Hex_5HexNAc_4$ | 13,967 | 13,971 | 13,971 |
| N-terminal peptide residues 1-63 (homoserine) plus $NeuAc_2Hex_5HexNAc_4$ | 9184 | 9185 | 9185 |
| Fucosylated N-terminal glycopeptide residues 1-63 (homoserine) plus $NeuAc_2Hex_5HexNAc_4Fuc$ | 9331 | 9331 | 9331 |
| Glycopeptide residue 64-220 (homoserine) plus $NeuAc_2Hex_5HexNAc_4$ | 20,170.5 | 20,174 | 20,175 |
| The 24aa signal peptide | ND | ND | ND |
| Peptides 1-63, 243-351 and 64-220 in non-glycosylated forms | ND | ND | ND |
| C-terminal peptide residues 386-394 | 970.5<br>486.0 (Doubly charged) | 970.7<br>486.0 (Doubly charged) | 970.8<br>486.4 (Doubly charged) |
| Confirmation of the sequence | 100% | 100% | 100% |

N-Linked Oligosaccharide Population Analysis

The purpose of the test was to obtain the profile of the oligosaccharides bound to the API and determine the API glycosylation sites, i.e. the points of binding of oligosaccharides to the polypeptide. Only N-linked oligosaccharides are evaluated because O-linked oligosaccharides are not known to exist in API.

Oligosaccharide analysis included enzymatic digestion of API samples with chymotrypsin and subsequent digestion with peptide N-glycosidase F (PNGase F), separation of the released carbohydrates from peptides using C18 Sep-pak cartridge, permethylation of the glycans and finally their analysis by Fast Atom Bombardment (FAB)-MS and MALDI-TOF MS. The results are presented in table 7 below.

TABLE 7

| N-Linked Oligosaccharide Population | | | |
|---|---|---|---|
| Glycans | Lot #6112006 m/z Signal | Lot #6113010, m/z Signal | Lot #6123010, m/z Signal |
| $NeuAc_2$ $Hex_5$•$HexNAc_4$ | 279 (Major Signal) | 279 (Major Signal) | 2793 (Major Signal) |
| $NeuAc_3$.$Hex_6$•$HexNAc_5$ | 3604 (Minor Signal) | 3604 (Minor Signal) | 3605 (Minor Signal) |

TABLE 7-continued

| N-Linked Oligosaccharide Population | | | |
|---|---|---|---|
| Glycans | Lot #6112006 m/z Signal | Lot #6113010, m/z Signal | Lot #6123010, m/z Signal |
| $NeuAc_2$ $Hex_5$•$HexNAc_4$.Fuc | 2969 (Minor Signal) | 2969 (Minor Signal) | 2968 (Minor Signal) |
| $NeuAc_3$.$Hex_6$•$HexNAc_5$•Fuc | 3779 (Minor Signal) | 3779 (Minor Signal) | 3779 (Minor Signal) |
| N-Glycosylation Sites | Asn-46, Asn-83 and Asn-247 | Asn-46, Asn-83 and Asn-247 | Asn-46, Asn-83 and Asn-247 |

Monosacccharide Composition Analysis

The monosacccharide composition of a glycoprotein is a basic characteristic of its oligosaccharide part. For monosaccharide analysis, the samples of the API lots were methanolysed, derivatised and analyzed by chromatography/mass spectrometry (GC/MS). The method allowed the estimation of the monosaccharides per mole of glycoprotein and, thus, the approximation of the total oligosaccharide percent. The monosaccharide composition of the three lots examined is shown in Table 8 below.

TABLE 8

| Monosaccharide Composition | | | | | | |
|---|---|---|---|---|---|---|
| | Lot #6112006 | | Lot #6113010 | | Lot #6123010 | |
| Monosaccharides | Monosaccharide nmoles present/mg of protein | Ratio (Mannose = 3.0) | Monosaccharide nmoles present/mg of protein | Ratio (Mannose = 3.0) | Monosaccharide nmoles present/mg of protein | Ratio (Mannose = 3.0) |
| Fuc | 7.7 | 0.1 | 12.0 | 0.2 | 10.4 | 0.2 |
| Man | 197 | 3.0 | 200 | 3.0 | 204 | 3.0 |
| Gal | 182 | 2.8 | 208 | 3.1 | 216 | 3.2 |

TABLE 8-continued

| Monosaccharide Composition | | | | | | |
|---|---|---|---|---|---|---|
| | Lot #6112006 | | Lot #6113010 | | Lot #6123010 | |
| Monosaccharides | Monosaccharide nmoles present/mg of protein | Ratio (Mannose = 3.0) | Monosaccharide nmoles present/mg of protein | Ratio (Mannose = 3.0) | Monosaccharide nmoles present/mg of protein | Ratio (Mannose = 3.0) |
| GalNAc | ND | / | ND | / | ND | / |
| GlcNAc | 125 | 1.9 | 222 | 3.3 | 242 | 3.6 |
| NeuAc | 93 | 1.4 | 128 | 1.9 | 98 | 1.4 |

Circular Dichroism

The purpose of the Circular Dichroism (CD) spectroscopy measurements was to characterize the secondary and tertiary structures of the API obtained by the process of the present invention. The CD of the API was measured in two regions: the near UV, 320-260 nm, and far UV, 260-180 nm. Far UV CD spectrum was used to determine α-helices, and near UV CD was used to characterize the tertiary structure.

Figure 3A:
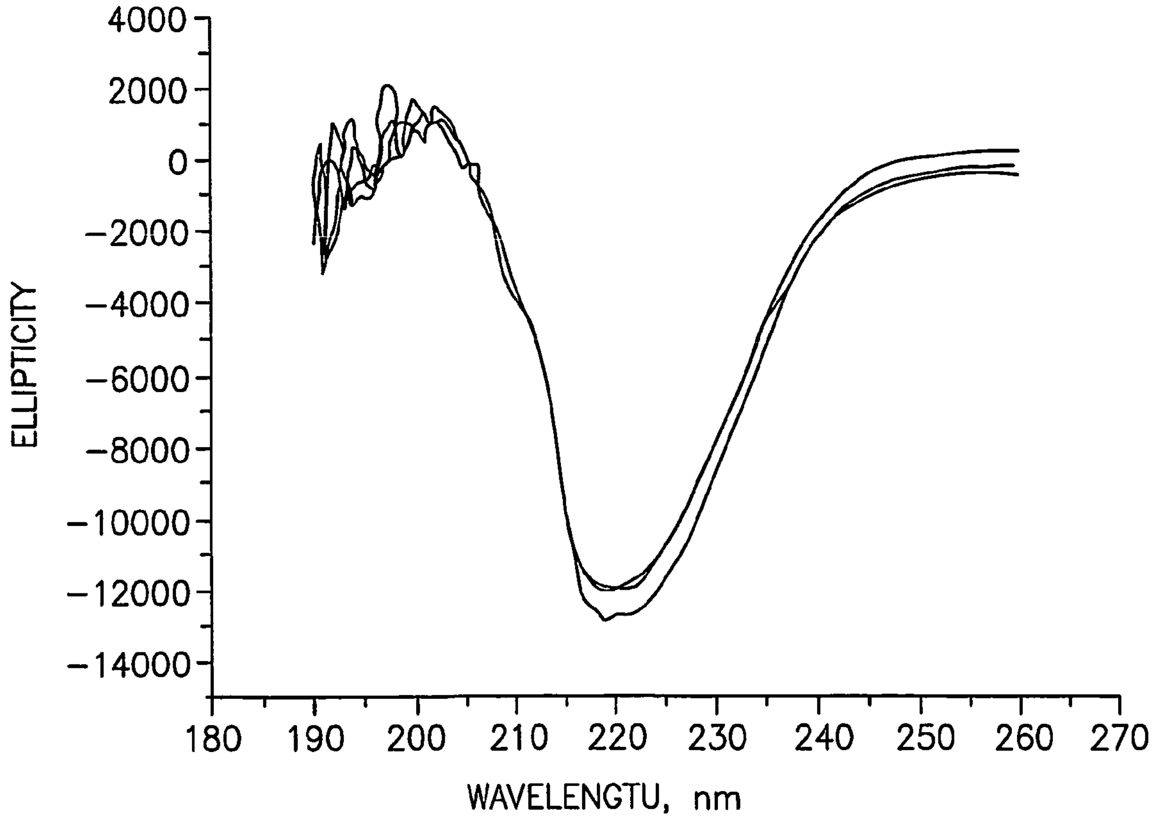
FIG. 3 shows far (FIG. 3A) and near (FIG. 3B) UV circular dichroism Spectra of API Lots 6112006, 6113010, 612301 and API Primary Reference Standard.
Figure 3B:
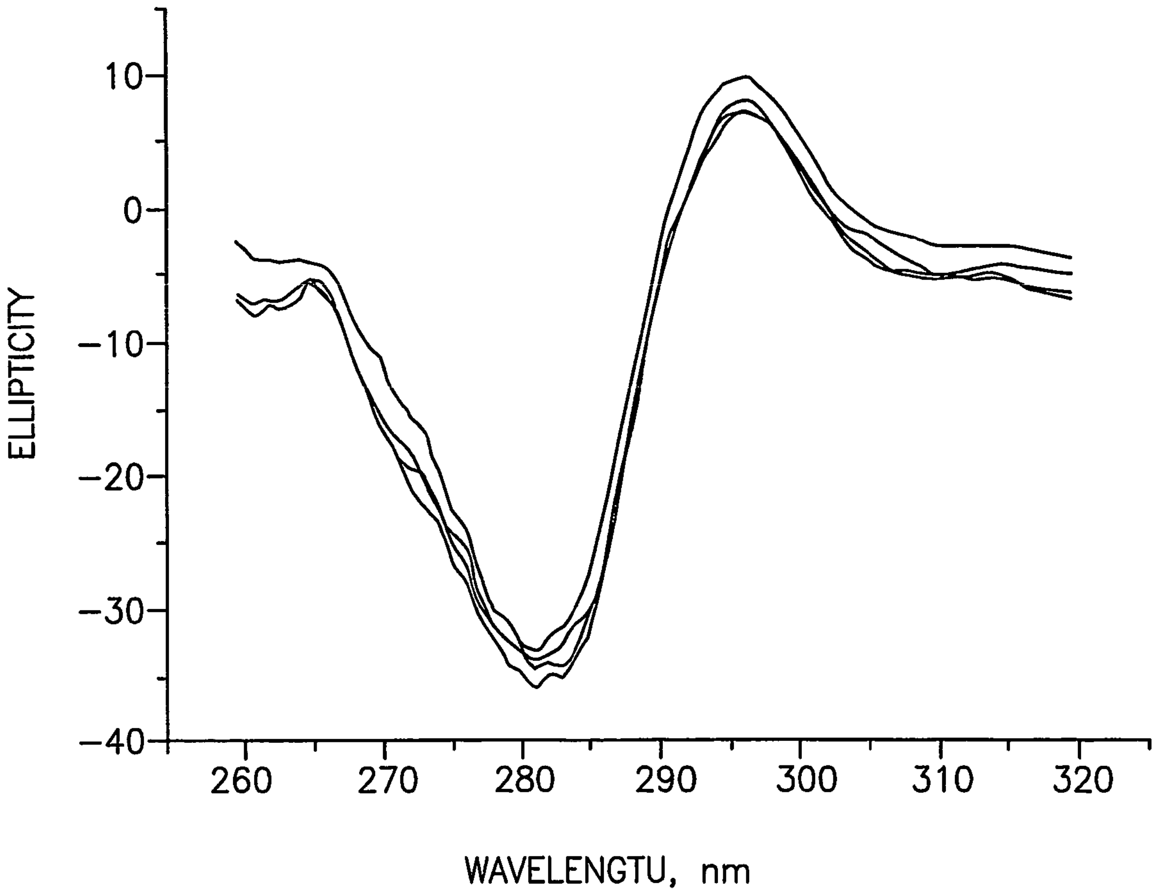

CD spectroscopy measures differences in the absorption of the left-handed polarized light versus right-handed polarized light, which arise due to structural asymmetry. The absence of regular structure results in zero CD intensity, while an ordered structure results in a spectrum, which can contain both positive and negative signals. Far and near UV CD Spectra of API Lots 6112006, 6113010, 612301 and API Primary Reference Standard #02/07 are shown in FIGS. 3A and B, respectively.

Example 10

API Stability

A. Stability of Typical API Pharmaceutical Preparation Comprising 2% API

Materials and Methods

The stability of API in the pharmaceutical preparation obtained by the process of the present invention was measured up to 36 months at storage temperature of 5±3° C., according to the following parameters as described in Table 9 below: appearance; content of active API; distribution of molecular size (concentration of API monomers and concentration of API aggregates. API aggregates are inactive); and pH.

API activity was assayed by the elastase inhibition assay as described above, and by the presence of API aggregates analyzed by analytical liquid chromatography [Size exclusion (SEC) HPLC] using a Zorbax GF-250 column. Total protein concentration was determined by absorbance at 280 nm.

Results

Stability of a typical API pharmaceutical preparation produced by the process of the present invention, containing 2% API, is shown in Table 9 below.

TABLE 9

| Stability of API stored at 5 ± 3° C. | | | | | | |
|---|---|---|---|---|---|---|
| | | Appearance | Active API | Distribution of Molecular size | | |
| Test Specification | | The solution is clear and colorless | content 2.0-2.4 g/100 ml | Polymer & aggregate < 10% | Monomer ≧ 90% | pH 6.8-7.2 |
| Start (May 8, 2000) | | Pass | 2.2 | 0.0 | 98.5 | 6.8 |
| 1 Month | Up* | Pass | 2.2 | 0.3 | 98.3 | 6.8 |
| (Jun.8, 2000) | Inv.** | Pass | 2.3 | 0.3 | 98.1 | 6.8 |
| 2 Months | Up* | Pass | 2.1 | 0.4 | 98.9 | 6.8 |
| (Jul. 8, 2000) | Inv.** | Pass | 2.1 | 0.4 | 98.8 | 6.8 |
| 3 Months | Up* | Pass | 2.0 | 0.4 | 98.7 | 6.8 |
| (Aug. 8, 2000) | Inv.** | Pass | 2.0 | 0.4 | 97.8 | 6.9 |
| 6 Months | Up* | Pass | 2.0 | 0.8 | 98.3 | 6.9 |
| (Nov. 8, 2000) | Inv.** | Pass | 2.1 | 0.8 | 98.2 | 6.8 |
| 9 Months | Up* | Pass | 2.0 | 1.0 | 99.0 | 6.8 |
| (Feb. 9, 2001) | Inv.** | Pass | 2.0 | 1.3 | 98.1 | 6.8 |
| 12 Months | Up* | Pass | 2.0 | 1.0 | 98.5 | 6.8 |
| (May 8, 2001) | Inv.** | Pass | 2.1 | 1.3 | 98.0 | 6.8 |
| 18 Months | Up* | Pass | 2.2 | 1.5 | 98.0 | 6.8 |
| (Nov. 8, 2001) | Inv.** | Pass | 2.2 | 1.2 | 98.8 | 6.8 |
| 24 Months | Up* | Pass | 1.9 | 9.3 | 90.7 | 6.8 |
| (May 8, 2002) | Inv.** | Pass | 1.9 | 9.4 | 90.6 | 6.8 |

TABLE 9-continued

Stability of API stored at 5 ± 3° C.

| | | Appearance | Active API | Distribution of Molecular size | | |
|---|---|---|---|---|---|---|
| Test Specification | | The solution is clear and colorless | content 2.0-2.4 g/100 ml | Polymer & aggregate < 10% | Monomer ≧ 90% | pH 6.8-7.2 |
| 36 Months | Up* | Pass | 2.0 | 11.0 | 89.0 | 6.8 |
| (May 8, 2003) | Inv.** | Pass | 2.0 | 11.0 | 89.0 | 6.8 |

*Up: Upright position
**Inv.: Inverted position

As shown in table 9, the API obtained by the process of the present invention is highly stable. As described herein above, a specific advantage of the pharmaceutical preparation of the present invention is that the highly purified, active API is also highly stable, in a ready to use liquid solution and without the presence of any protein stabilizer.

B. Stability of Concentrated API Pharmaceutical Preparation Comprising 5-20% API The purpose of the study was to determine API stability under conditions favorable for Aerosol production. These conditions include increased API concentration to about 10%, and preferably up to 20%. The stability of the concentrated solutions was determined in the cold (2-8° C.) and at ambient temperature (~25° C.). Stability was examined by the formation of aggregates (aggregate forms of API are inactive) and by measuring API activity as described herein above.

Materials and Methods

API solutions in a protein concentration range of 5%-20% were prepared from a 2% API preparation (lot no. 6013009, Kamada, Israel). The solutions were incubated in the absence of Tween 80 and in the presence of Tween 80 at concentrations of 0%, 0.01%, 0.05% and 0.1%; one set was kept under refrigeration at 2° C.-8° C. and the other set was kept at 20° C.-25° C. The samples of both sets were analyzed at times zero, 4 weeks, 8 weeks and 12 weeks for protein content, API activity, concentration of API monomers and concentration of API aggregates.

The 2% API solution was concentrated from 2% API to ~20% and higher, by an A.G. Technology NMWC 10000 ultrafilter (UFP-10C-4X2A). Based on the starting volume and API concentration, aliquots of concentrated solution were withdrawn at various stages during ultrafiltration. The following API concentrates were obtained: 6.34%, 12.2%, 18.1%, and 22.84%. These solutions served for the preparation of the final solutions used in the study, containing 5%, 10%, 15%, and 20% protein.

Results

Stability of concentrated API preparations prepared as described below and kept at 20-25° C. is shown in Table 10 below.

TABLE 10

Stability of concentrated API preparations stored at 20-25° C.

| Group Description | Sample I.D.(*) | Protein (mg/mL) | API (mg/mL) | Specific API Activity | HPLC % API Monomer | HPLC % API Aggregates |
|---|---|---|---|---|---|---|
| 5% API | $5_0$ a | 51.92 | 48.8 | 0.94 | 96.8 | 3.23 |
| No Tween | $5_{30}$ a T-1 | 49.06 | 50.4 | 1.03 | 96.54 | 3.48 |
| | $5_{60}$ a T-1 | N.D. | N.D. | N.D. | N.D. | N.D. |
| | $5_{90}$ a T-1 | 50.9 | 45.6 | 0.90 | 95.01 | 4.95 |
| 5% API | $5_0$ b | 50.93 | 48.2 | 0.95 | 97.1 | 2.81 |
| 0.01% Tween | $5_{30}$ b T-1 | 49.45 | 50.3 | 1.02 | 94.82 | 5.19 |
| | $5_{60}$ b T-1 | N.D. | N.D. | N.D. | N.D. | N.D. |
| | $5_{90}$ b T-1 | 51.6 | 46.8 | 0.91 | 94.43 | 5.42 |
| 5% API | $5_0$ c | 51.87 | 49.3 | 0.95 | 96.7 | 3.30 |
| 0.05% Tween | $5_{30}$ c T-1 | 50.49 | 53.3 | 1.05 | 95.41 | 4.60 |
| | $5_{60}$ c T-1 | 48.9 | 46.9 | 0.96 | 93.82 | 6.10 |
| | $5_{90}$ c T-1 | 51.3 | 44.0 | 0.86 | 92.28 | 7.56 |
| 5% API | $5_0$ d | 51.81 | 47.8 | 0.92 | 96.4 | 3.62 |
| 0.1% Tween | $5_{30}$ d T-1 | 48.90 | 51.5 | 1.05 | 96.40 | 3.60 |
| | $5_{60}$ d T-1 | 48.9 | 44.3 | 0.90 | 93.59 | 6.29 |
| | $5_{90}$ d T-1 | 51.0 | 42.0 | 0.82 | 91.04 | 8.90 |
| 10% API | $10_0$ a | 95.48 | 95.3 | 1.00 | 96.4 | 3.56 |
| No Tween | $10_{30}$ a T-1 | 97.18 | 102.6 | 1.05 | 95.22 | 4.78 |
| | $10_{60}$ a T-1 | 96.7 | 90.2 | 0.93 | 93.89 | 6.08 |
| | $10_{90}$ a T-1 | 93.8 | 90.5 | 0.97 | 92.72 | 7.21 |
| 10% API | $10_0$ b | 95.76 | 95.0 | 0.99 | 96.4 | 3.62 |
| 0.01% Tween | $10_{30}$ b T-1 | 97.40 | 106.4 | 1.09 | 95.11 | 4.89 |
| | $10_{60}$ b T-1 | 96.2 | 90.9 | 0.94 | 93.98 | 5.98 |
| | $10_{90}$ b T-1 | 95.3 | 89.0 | 0.93 | 92.07 | 7.85 |
| 10% API | $10_0$ c | 97.08 | 93.6 | 0.96 | 96.5 | 3.55 |
| 0.05% Tween | $10_{30}$ c T-1 | 98.17 | 106.2 | 1.08 | 94.35 | 5.66 |

TABLE 10-continued

Stability of concentrated API preparations stored at 20-25° C.

| Group Description | Sample I.D.(*) | Protein (mg/ml) | API (mg/ml) | Specific API Activity | HPLC (% API Mono.) | HPLC (% API Aggreg.) |
|---|---|---|---|---|---|---|
| | $10_{60}$ c T-1 | 97.9 | 86.7 | 0.88 | 92.36 | 7.65 |
| | $10_{90}$ c T-1 | 96.5 | 89.6 | 0.93 | 90.72 | 9.22 |
| 10% API | $10_0$ d | 98.01 | 96.4 | 0.98 | 96.2 | 3.81 |
| 0.1% Tween | $10_{30}$ d T-1 | 97.29 | 102.7 | 1.05 | 93.61 | 6.39 |
| | $10_{60}$ d T-1 | 96.3 | 91.7 | 0.95 | 92.39 | 7.61 |
| | $10_{90}$ d T-1 | 96.9 | 85.3 | 0.88 | 89.43 | 10.49 |
| 15% API | $15_0$ a | 147.50 | 147.2 | 1.00 | 96.1 | 3.90 |
| No Tween | $15_{30}$ a T-1 | 148.60 | 139.2 | 0.94 | 93.00 | 7.01 |
| | $15_{60}$ a T-1 | 153.5 | 145.9 | 0.95 | 92.29 | 7.67 |
| | $15_{90}$ a T-1 | 151.2 | 134.2 | 0.89 | 89.56 | 10.36 |
| 15% API | $15_0$ b | 148.60 | 151.6 | 1.02 | 95.9 | 3.80 |
| 0.01% Tween | $15_{30}$ b T-1 | 152.00 | 139.2 | 0.92 | 92.95 | 7.06 |
| | $15_{60}$ b T-1 | 152.0 | 144.5 | 0.95 | 91.58 | 8.40 |
| | $15_{90}$ b T-1 | 151.1 | 134.6 | 0.89 | 88.46 | 11.39 |
| 15% API | $15_0$ c | 150.10 | 149.4 | 0.99 | 96.0 | 4.00 |
| 0.05% Tween | $15_{30}$ c T-1 | 150.20 | 137.6 | 0.92 | 92.07 | 7.94 |
| | $15_{60}$ c T-1 | 154.6 | 143.9 | 0.93 | 90.05 | 9.82 |
| | $15_{90}$ c T-1 | 148.4 | 145.4 | 0.98 | 86.50 | 13.37 |
| 15% API | $15_0$ d | 149.00 | 154.7 | 1.04 | 96.2 | 3.74 |
| 0.1% Tween | $15_{30}$ d T-1 | 152.60 | 142.4 | 0.93 | 91.80 | 8.21 |
| | $15_{60}$ d T-1 | 154.4 | 143.0 | 0.93 | 89.27 | 10.65 |
| | $15_{90}$ d T-1 | 147.7 | 140.5 | 0.95 | 85.37 | 14.38 |
| 20% API | $20_0$ a | 186.8 | 192.3 | 1.03 | 95.6 | 4.44 |
| No Tween | $20_{30}$ a T-1 | 190.7 | 169.0 | 0.89 | 90.95 | 8.98 |
| | $20_{60}$ a T-1 | 197.8 | 159.0 | 0.80 | 89.19 | 10.76 |
| | $20_{90}$ a T-1 | 193.1 | 159.0 | 0.82 | 84.93 | 14.98 |
| 20% API | $20_0$ b | 191.9 | 186.5 | 0.97 | 95.4 | 4.59 |
| 0.01% Tween | $20_{30}$ b T-1 | 202.9 | 175.1 | 0.86 | 90.03 | 9.60 |
| | $20_{60}$ b T-1 | 194.7 | 159.1 | 0.82 | 85.86 | 14.04 |
| | $20_{90}$ b T-1 | 192.1 | 161.1 | 0.84 | 85.19 | 14.70 |
| 20% API | $20_0$ c | 194.6 | 192.2 | 0.99 | 95.7 | 4.34 |
| 0.05% Tween | $20_{30}$ c T-1 | 186.4 | 169.7 | 0.91 | 89.85 | 10.06 |
| | $20_{60}$ c T-1 | 187.0 | 160.1 | 0.86 | 87.02 | 12.98 |
| | $20_{90}$ c T-1 | 195.4 | 160.9 | 0.82 | 82.17 | 17.75 |
| 20% API | $20_0$ d | 192.3 | 190.0 | 0.99 | 95.4 | 4.63 |
| 0.1% Tween | $20_{30}$ d T-1 | 199.2 | 171.8 | 0.86 | 88.83 | 11.10 |
| | $20_{60}$ d T-1 | 196.5 | 160.8 | 0.82 | 88.20 | 11.75 |
| | $20_{90}$ d T-1 | 189.0 | 167.8 | 0.89 | 81.39 | 18.58 |

(*) Sample Codes:
I. % —20, 15, 10, 5API
II. Subscripts: 0 - time zero, 30 - 4 weeks, 60 - 8 weeks, 90 - 12 weeks
III. a: no Tween, b: 0.01% Tween, c: 0.05% Tween, d: 0.1% Tween
IV. T-1: 25° C., T-2: 2-8° C.

Stability of concentrated API preparations prepared as described below and kept in the cold at 2-8° C. is shown in Table 11 below.

TABLE 11

Stability of concentrated API preparations stored at 2-8° C.

| Group Description | Sample I.D.(*) | Protein (mg/mL) | API (mg/mL) | Specific API Activity | HPLC (% API Mono.) | HPLC (% API Aggreg.) |
|---|---|---|---|---|---|---|
| 5% API | $5_0$ a | 51.92 | 48.8 | 0.94 | 96.8 | 3.23 |
| No Tween | $5_{30}$ a T-2 | 48.73 | 50.3 | 1.03 | 96.85 | 3.15 |
| | $5_{60}$ a T-2 | 49.2 | 50.4 | 1.02 | 96.46 | 3.55 |
| | $5_{90}$ a T-2 | 50.4 | 48.6 | 0.97 | 96.14 | 3.87 |
| 5% API | $5_0$ b | 50.93 | 48.2 | 0.95 | 97.1 | 2.81 |
| 0.01% Tween | $5_{30}$ b T-2 | 49.12 | 52.1 | 1.06 | 96.58 | 3.43 |
| | $5_{60}$ b T-2 | 49.4 | 48.6 | 0.98 | 95.83 | 4.18 |
| | $5_{90}$ b T-2 | 50.8 | 45.2 | 0.89 | 95.55 | 4.46 |
| 5% API | $5_0$ c | 51.87 | 49.3 | 0.95 | 96.7 | 3.30 |
| 0.05% Tween | $5_{30}$ c T-2 | 49.67 | 52.1 | 1.05 | 95.60 | 4.41 |
| | $5_{60}$ c T-2 | 49.3 | 48.4 | 0.98 | 94.89 | 5.12 |
| | $5_{90}$ c T-2 | 49.4 | 48.6 | 0.98 | 93.56 | 6.45 |

TABLE 11-continued

Stability of concentrated API preparations stored at 2-8° C.

| Group Description | Sample I.D.(*) | Protein (mg/mL) | API (mg/mL) | Specific API Activity | HPLC (% API Mono.) | HPLC (% API Aggreg.) |
|---|---|---|---|---|---|---|
| 5% API | $5_0$ d | 51.81 | 47.8 | 0.92 | 96.4 | 3.62 |
| 0.1% Tween | $5_{30}$d T-2 | 49.06 | 52.8 | 1.08 | 94.52 | 5.35 |
| | $5_{60}$ d T-2 | 49.4 | 47.2 | 0.96 | 92.94 | 7.07 |
| | $5_{90}$ d T-2 | 49.9 | 46.2 | 0.93 | 91.68 | 8.32 |
| 10% API | $10_0$ a | 95.48 | 95.3 | 1.00 | 96.4 | 3.56 |
| No Tween | $10_{30}$ a T-2 | 96.58 | 103.9 | 1.08 | 96.18 | 3.82 |
| | $10_{60}$ a T-2 | 96.9 | 94.1 | 0.97 | 95.53 | 4.48 |
| | $10_{90}$ a T-2 | 96.6 | 99.7 | 1.03 | 95.03 | 4.89 |
| 10% API | $10_0$ b | 95.76 | 95.0 | 0.99 | 96.4 | 3.62 |
| 0.01% Tween | $10_{30}$ b T-2 | 97.02 | 108.0 | 1.11 | 96.06 | 3.95 |
| | $10_{60}$ b T-2 | 96.6 | 95.7 | 0.99 | 95.36 | 4.65 |
| | $10_{90}$ b T-2 | 97.3 | 97.4 | 1.00 | 94.15 | 5.82 |
| 10% API | $10_0$ c | 97.08 | 93.6 | 0.96 | 96.5 | 3.55 |
| 0.05% Tween | $10_{30}$c T-2 | 97.73 | 98.40 | 1.01 | 95.18 | 4.72 |
| | $10_{60}$ c T-2 | 97.5 | 96.5 | 0.99 | 94.82 | 5.19 |
| | $10_{90}$ c T-2 | 97.3 | 97.9 | 1.01 | 93.32 | 6.64 |
| 10% API | $10_0$ d | 98.01 | 96.4 | 0.98 | 96.2 | 3.81 |
| 0.1% Tween | $10_{30}$d T-2 | 96.96 | 106.7 | 1.10 | 94.59 | 5.41 |
| | $10_{60}$ d T-2 | 99.7 | 97.5 | 0.98 | 93.66 | 6.35 |
| | $10_{90}$ d T-2 | 96.9 | 93.9 | 0.97 | 91.37 | 8.51 |
| 15% API | $15_0$ a | 147.50 | 147.2 | 1.00 | 96.1 | 3.90 |
| No Tween | $15_{30}$ a T-2 | 150.00 | 150.7 | 1.00 | 94.95 | 5.06 |
| | $15_{60}$ a T-2 | 150.6 | 145.5 | 0.97 | 95.17 | 4.85 |
| | $15_{90}$ a T-2 | 146.7 | 149.7 | 1.02 | 93.88 | 6.06 |
| 15% API | $15_0$ b | 148.60 | 151.6 | 1.02 | 95.9 | 3.80 |
| 0.01% Tween | $15_{30}$ b T-2 | 150.40 | 145.0 | 0.96 | 94.90 | 5.21 |
| | $15_{60}$ b T-2 | 149.1 | 149.3 | 1.00 | 94.26 | 5.75 |
| | $15_{90}$ b T-2 | 146.6 | 153.0 | 1.04 | 93.11 | 6.90 |
| 15% API | $15_0$ c | 150.10 | 149.4 | 0.99 | 96.0 | 4.00 |
| 0.05% Tween | $15_{30}$ c T-2 | 150.20 | 138.9 | 0.92 | 95.00 | 4.84 |
| | $15_{60}$ c T-2 | 152.1 | 150.1 | 0.99 | 93.67 | 6.33 |
| | $15_{90}$ c T-2 | 146.7 | 149.5 | 1.02 | 92.24 | 7.77 |
| 15% API | $15_0$ d | 149.00 | 154.7 | 1.04 | 96.2 | 3.74 |
| 0.1% Tween | $15_{30}$ d T-2 | 149.00 | 141.8 | 0.95 | 94.90 | 5.08 |
| | $15_{60}$ d T-2 | 152.5 | 146.8 | 0.96 | 93.18 | 6.83 |
| | $15_{90}$ d T-2 | 146.9 | 148.0 | 1.01 | 91.10 | 8.92 |
| 20% API | $20_0$ a | 186.8 | 192.3 | 1.03 | 95.6 | 4.44 |
| No Tween | $20_{30}$ a T-2 | 194.7 | 185.8 | 0.95 | 94.03 | 5.99 |
| | $20_{60}$ a T-2 | 194.5 | 190.9 | 0.98 | 93.90 | 6.11 |
| | $20_{90}$ a T-2 | 190.3 | 194.8 | 1.02 | 92.33 | 7.47 |
| 20% API | $20_0$ b | 191.9 | 186.5 | 0.97 | 95.4 | 4.59 |
| 0.01% Tween | $20_{30}$ b T-2 | 200.3 | 189.9 | 0.95 | 94.03 | 5.97 |
| | $20_{60}$ b T-2 | 192.9 | 194.9 | 1.01 | 93.55 | 6.46 |
| | $20_{90}$ b T-2 | 189.8 | 188.8 | 0.99 | 91.85 | 7.87 |
| 20% API | $20_0$ c | 194.6 | 192.2 | 0.99 | 95.7 | 4.34 |
| 0.05% Tween | $20_{30}$ c T-2 | 207.7 | 193.6 | 0.93 | 93.75 | 6.26 |
| | $20_{60}$ c T-2 | 189.7 | 202.4 | 1.07 | 92.36 | 7.65 |
| | $20_{90}$ c T-2 | 196.0 | 189.9 | 0.97 | 91.25 | 8.57 |
| 20% API | $20_0$ d | 192.3 | 190.0 | 0.99 | 95.4 | 4.63 |
| 0.1% Tween | $20_{30}$d T-2 | 198.2 | 190.3 | 0.96 | 93.33 | 6.67 |
| | $20_{60}$ d T-2 | 190.2 | 202.0 | 1.06 | 92.69 | 7.32 |
| | $20_{90}$ d T-2 | 196.4 | 185.8 | 0.95 | 90.10 | 9.53 |

(*) Sample Codes:

I. 5, 10, 15, 20 —% API

II. Subscripts: 0 - time zero, 30 - 4 weeks, 60 - 8 weeks, 90 - 12 weeks

III. a: no Tween, b: 0.01% Tween, c: 0.05% Tween, d: 0.1% Tween

IV. T-1: 25° C., T-2: 2-8° C.

The data shown in the above tables demonstrate that the decline in the percentage of the active monomeric form of API is not always reflected by the activity data obtained by the elastase assay. Therefore, API activity was evaluated by the percentage of API monomers measured by HPLC.

Graphic presentation (not shown) was used to estimate the stability of API stored in the above-described conditions after 12 and 24. The results are summarized in Table 12 below.

TABLE 12

Expected percentage of API monomers after storage for 12 month at 2-8° C.

| | | Percent of API Monomer | | |
|---|---|---|---|---|
| Concentration of API, % | Concentration of Tween 80, % | Time zero | 12 months | 24 months |
| 5 | 0 | 97.0 | 94.1 | 91.3 |
| | 0.01 | | 90.2 | 83.1 |
| | 0.05 | | 84.3 | 71.7 |
| | 0.1 | | 77.0 | 57.4 |
| 10 | 0 | 96.6 | 90.9 | 85.2 |
| | 0.01 | | 87.7 | 78.7 |
| | 0.05 | | 84.6 | 72.6 |
| | 0.1 | | 78.0 | 59.4 |
| 15 | 0 | 96.2 | 88.3 | 80.4 |
| | 0.01 | | 84.1 | 72.0 |
| | 0.05 | | 80.6 | 65.0 |
| | 0.1 | | 75.4 | 54.6 |
| 20 | 0 | 95.6 | 84.2 | 72.8 |
| | 0.01 | | 82.2 | 70.0 |
| | 0.05 | | 78.3 | 61.0 |
| | 0.1 | | 76.6 | 57.6 |

CONCLUSIONS

The use of ultrafiltration for concentrating the 2% solution obtained by the process of the present caused some generation of aggregates. Thus, the concentrated solutions already contained higher aggregate concentration at the beginning of the assay compared to the aggregate concentration in the initial 2% solution. The presence of Tween 80 in the concentrated solution caused an increase in aggregation through the storage period. This effect is concentration dependent. In addition, increase in the initial concentration of API caused an increase in the formation of aggregates. This phenomenon was observed throughout the assay, in both temperature conditions and with or without Tween 80. However, general analyses of all the data obtained clearly show that concentrated solutions of API stored at 2-8° C. are essentially stable for at least 3 months, and will maintain a good potency at this temperature for one year, even in the presence of some Tween 80. Therefore, the ready to use API-containing fluid preparation produced by the process of the present invention is highly suitable for the preparation of pharmaceutical compositions to be administered parenterally as well as by inhalation.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A large scale process for purifying alpha-1 proteinase inhibitor (API) from an unpurified mixture of proteins comprising:

(a) dispersing the unpurified mixture of proteins containing API in an aqueous medium; (b) removing a portion of contaminating lipids and proteins by adding a lipid removal agent to the aqueous dispersion and precipitating the portion of contaminating proteins from said aqueous dispersion;

(c) loading an API-containing supernatant of step (b) containing API on a first anion exchange resin with a buffer solution having pH and conductivity such that API is retained on the first anion exchange resin;

(d) eluting an API-containing fraction from said first anion exchange resin with a same type of buffer as in step (c) having adjusted pH and conductivity;

(e) loading an API-containing fraction of step (d) on a cation exchange resin in said same type of buffer having appropriate pH and conductivity such that API is not retained on the cation exchange resin;

(f) collecting a flow-through of step (e) that contains API;

(g) loading an API-containing fraction of step (f) on a second anion exchange resin with said same type of buffer having appropriate pH and conductivity such that API binds to the second anion exchange resin; and (h) eluting API from said second anion exchange resin with said same type of buffer having adjusted pH and conductivity to obtain a purified active API which is stable without the addition of a protein stabilizer.

2. The process of claim 1, wherein the API comprises at least 90% active API out of the total API recovered.

3. The process of claim 2, wherein the API comprises at least 95% active API out the total API recovered.

4. The process of claim 1, wherein the API comprises at least 90% API out of the total protein recovered.

5. The process of claim 4, wherein the API comprises at least 95% API out of the total protein recovered.

6. The process of claim 1, wherein the buffer solution is other than citrate based buffer.

7. The process of claim 1, wherein the buffer solution is acetate-based buffer.

8. The process of claim 1 further comprising a viral inactivation step.

9. The process of claim 8 wherein the viral inactivation step comprises adding a solvent and a detergent to the API of step (f) collected from the cation exchange resin.

10. The process of claim 9 wherein the detergent is a non-ionic detergent.

11. The process of claim 1, further comprising a viral removal step.

12. The process of claim 11, wherein the viral removing step comprises nanofiltration.

13. The process of claim 1, wherein the unpurified mixture of proteins is selected from the group consisting of Cohn Fractions, human blood plasma and plasma fractions.

14. The process of claim 13 wherein the unpurified mixture of proteins is Cohn fraction IV-paste.

15. The process of claim 1 wherein the lipid removing agent is silicon dioxide.

16. The process of claim 1 wherein the portion of contaminating lipids and proteins is precipitated by polyalkylene glycol.

17. The process of claim 16, wherein the polyalkylene glycol is polyethylene glycol.

18. The process of claim 16 wherein precipitation is performed at a pH from about 5.0 to about 6.5.

19. The process of claim 1, wherein the first and the second anion exchange resin is a DEAE-Sepharose resin.

20. The process of claim 1 wherein the cation exchange resin is Carboxymethyl-Sepharose resin.

21. The process of claim 1, wherein the pH of the buffer solution is at a pH of between 5.5 and 6.5 for the elution of the API from the first and the second anion exchange resin.

22. The process of claim 1, further comprising changing the ionic composition of the solution containing the purified, active API to contain a physiologically compatible ion and sterilizing the resulted solution.

23. The process of claim 22, wherein the solution containing API is concentrated before loading on the ion exchange resin.

24. The process of claim 22, wherein the physiologically compatible ion is selected from the group consisting of a phosphate ion, a chloride ion and combinations thereof.

25. The process of claim 1 which further comprises formulating a pharmaceutical preparation comprising the purified active stable API as an active ingredient.

26. The process of claim 25 wherein the pharmaceutical preparation is formulated with the solution of purified, active stable API and is sterilized.

27. The process of claim 26 wherein the preparation is formulated to have a pH in the range of 6.5-7.5.

28. The process of claim 26 wherein the preparation is formulated to have a protein concentration between about 1% to about 3%.

29. The process of claim 26 wherein the preparation is formulated to be devoid of any protein stabilizer.

30. The process of claim 29 wherein the preparation is formulated to have the API stable for at least 3 months when the pharmaceutical preparation is stored at a temperature of between 20° C. to 25° C.

31. The process of claim 29 wherein the preparation is formulated to have the API stable for at least 12 to 36 months when the pharmaceutical composition is stored at a temperature of between 2° C. to 8° C.

32. The process of claim 25 wherein the preparation is formulated to also have an excipient, diluent or a carrier.

33. The process of claim 25 wherein the preparation is formulated to be administered intravenously.

34. The process of claim 25 wherein the preparation is formulated to be administered by inhalation.

35. The process of claim 25 which further comprises treating a subject in need thereof by administering the pharmaceutical preparation so that the subject receives a therapeutically effective amount of API.

36. The process of claim 35, wherein the subject is treated for a disease or disorder selected from the group consisting of pulmonary emphysema, chronic obstructive pulmonary disorder, cystic fibrosis associated lung diseases and disorders, psoriasis and atopic dermatitis.

37. The process of claim 35, wherein the subject is treated for pulmonary emphysema.

38. The process of claim 35, wherein the subject is treated for cystic fibrosis associated lung disease or disorder.

* * * * *

UNITED STATES PATENT AND TRADEMARK OFFICE

CERTIFICATE OF CORRECTION

PATENT NO. : 7,879,800 B2
APPLICATION NO. : 10/572523
DATED : February 1, 2011
INVENTOR(S) : Bauer It is certified that error appears in the above-identified patent and that said Letters Patent is hereby corrected as shown below:

Column 36:
Line 9 (claim 1, line 5), after "API in an aqueous medium;" start a new subparagraph with "(b) removing a portion of".

Signed and Sealed this
Eighth Day of March, 2011

David J. Kappos
*Director of the United States Patent and Trademark Office*